(12) United States Patent
Huffman

(10) Patent No.: US 8,948,496 B2
(45) Date of Patent: Feb. 3, 2015

(54) DYNAMIC TRANSFER OF THREE-DIMENSIONAL IMAGE DATA

(75) Inventor: John C. Huffman, Portland, CA (US)

(73) Assignee: Koninklijke Philips N.V., Eindhoven (NL)

( * ) Notice: Subject to any disclaimer, the term of this patent is extended or adjusted under 35 U.S.C. 154(b) by 773 days.

(21) Appl. No.: 13/058,545

(22) PCT Filed: Aug. 11, 2009

(86) PCT No.: PCT/IB2009/053551
§ 371 (c)(1),
(2), (4) Date: Feb. 11, 2011

(87) PCT Pub. No.: WO2010/023580
PCT Pub. Date: Mar. 4, 2010

(65) Prior Publication Data
US 2011/0142321 A1  Jun. 16, 2011

Related U.S. Application Data

(60) Provisional application No. 61/093,063, filed on Aug. 29, 2008.

(51) Int. Cl.
*G06K 9/00* (2006.01)
*H04N 21/2343* (2011.01)
(Continued)

(52) U.S. Cl.
CPC . *H04N 19/00818* (2013.01); *H04N 21/234327* (2013.01); *H04N 21/845* (2013.01);
(Continued)

(58) Field of Classification Search
USPC .................. 382/131, 154, 170, 232, 240, 227
See application file for complete search history.

(56) References Cited

U.S. PATENT DOCUMENTS 6,711,297 B1    3/2004  Chang et al.
6,925,208 B1 *  8/2005  Huffman .................. 382/232
(Continued)

FOREIGN PATENT DOCUMENTS

JP    2002165217 A    6/2002
JP    2003263651 A    9/2003
(Continued)

OTHER PUBLICATIONS

Joshi, R. L.; On-demand rendering of an oblique slice through 3D volumetric data using JPEG2000 client-server framework; 2006; Proc. of SPIE-Medical Imaging; vol. 6145; No. 614508; 12 pages.
(Continued)

*Primary Examiner* — Gregory M Desire

(57) ABSTRACT

A method for transferring volumetric image data from a server to at least one client comprising: transforming said volumetric images into a hierarchical representation comprising a plurality of coefficients, said hierarchical representation comprising a plurality of levels of essentially non-redundant data, wherein a level of said hierarchical representation comprises transform data sufficient to reconstruct said images at a resolution corresponding to said level; partitioning said coefficients into a plurality of voxels, each voxel comprising "n" coefficients in a horizontal direction, "m" coefficients in a vertical direction, and "P" coefficients in a depth direction; requesting, from a client to a server, transform data in the form of voxels from one or more levels of said hierarchical representation necessary to reconstruct at least a portion of said source volume; transferring, from a client to a server, a request for coefficients of at least a portion of said volumetric image; transferring, from said server to said client, at least one voxel in response to said request; and reconstructing, at said client, volumetric views of said volume images from said transferred at least one voxel.

11 Claims, 15 Drawing Sheets

(51) Int. Cl.
  *H04N 21/845* (2011.01)
  *H04N 21/658* (2011.01)
  *H04N 19/164* (2014.01)
  *H04N 19/64* (2014.01)
  *H04N 19/63* (2014.01)
  *H04N 7/173* (2011.01)
  *H04N 21/4728* (2011.01)
  *H04N 19/62* (2014.01)
  *H04N 21/2662* (2011.01)
  *H04N 21/81* (2011.01)
  *H04N 19/17* (2014.01)
  *H04N 19/129* (2014.01)
  *H04N 19/162* (2014.01)
  *G06F 19/00* (2011.01)

(52) U.S. Cl.
  CPC ..... *H04N21/6581* (2013.01); *H04N 19/00236* (2013.01); *H04N 19/0083* (2013.01); *H04N 7/17327* (2013.01); *H04N 21/4728* (2013.01); *H04N 19/00806* (2013.01); *H04N 21/2662* (2013.01); *H04N 21/8146* (2013.01); *H04N 19/0026* (2013.01); *H04N 19/00109* (2013.01); *H04N 19/0023* (2013.01); *G06F 19/321* (2013.01)
  USPC .......................... 382/154; 382/227; 382/240

(56) References Cited

U.S. PATENT DOCUMENTS

| | | | |
|---|---|---|---|
| 7,031,533 B2 * | 4/2006 | Felts et al. | 382/240 |
| 8,494,245 B2 * | 7/2013 | Liao et al. | 382/131 |
| 2005/0111746 A1 | 5/2005 | Kumar et al. | |
| 2007/0217676 A1 * | 9/2007 | Grauman et al. | 382/170 |
| 2010/0033482 A1 * | 2/2010 | Zhou et al. | 345/424 |
| 2010/0135544 A1 * | 6/2010 | Mattiuzzi et al. | 382/128 |
| 2011/0142321 A1 * | 6/2011 | Huffman | 382/131 |

FOREIGN PATENT DOCUMENTS

| | | |
|---|---|---|
| JP | 2006323653 A | 11/2006 |
| JP | 2008146473 A | 6/2008 |
| JP | 2011524483 A | 9/2011 |

OTHER PUBLICATIONS

Lalgudi, H. G., et al.; Four-Dimensional Compression of fMRI Using JPEG2000; 2005; Proc. of SPIE-Image Processing; vol. 5747:1028-1037.

* cited by examiner

DYNAMIC TRANSFER OF THREE-DIMENSIONAL IMAGE DATA

The following disclosure is related to the image processing arts, image transfer arts, data networking arts, medical imaging arts, medical diagnostic arts, and so forth. The following disclosure finds general application in distribution and processing of three-dimensional or volumetric images, and is described with illustrative reference to distribution and processing of medical images for diagnostic, clinical, preclinical, and other applications.

Slice-based scanners, such as computed tomography (CT) scanners are commonly used for acquiring three-dimensional or volumetric images of patients organized into two-dimensional slices that are successively stacked to define a three-dimensional volume. Some imaging modalities, such as magnetic resonance (MR) imaging, can acquire three-dimensional image data that is natively segregated into successively acquired slices, or is acquired along non-planar trajectories. However, even in MR imaging, it is conventional to organize the image data into a stack of successive slices defining a three-dimensional volume. The resultant image data sets acquired from increasingly sophisticated CT, MR and other volumetric medical imaging modality scanners contain thousands of individual image slices, each of which comprises thousands or more pixels. After acquiring image slices, medical personnel have traditionally printed out the slices, or selected slices of interest on film, using a printer or other marking engine.

More recently, the images have become stackable sequentially on a computer display using softcopy computer based imaging. This technique of displaying stacked images on a computer display provides the physician or healthcare professional a means to scroll through and rapidly view the images, in a pseudo-volume technique. This is accomplished through a Picture Archiving and Communication System (PACS). In a typical PACS arrangement, the images are stored remotely on a PACS server, and the radiologist or doctor is located at his or her office computer or another client device connected with the PACS server over the conventional hospital network or over a dedicated PACS network. The radiologist or doctor will open one patient study at a time from a list of patient studies in a worklist and view a complete image of the relevant anatomical feature to be studied (e.g., a CT image of the whole brain of a patient) in order to obtain anatomical orientation. Such a "whole-image" representation is preferably displayed in low resolution. The user will then scroll through the stacks of image slices until medically relevant features are suspected or found. However, certain medically relevant features, such as tumors, nodules, or the like, tend to be small and of relatively low contrast. Accordingly, on any particular image slice having or suspected of having a medically relevant feature, the radiologist or doctor will rapidly "zoom in" at high resolution on locations likely to contain features of interest. The slice-based paradigm for image viewing and processing has become increasingly difficult to employ as the size of image data sets has increased due to higher scanner resolution, faster acquisition rates, and other factors. Moreover, multi-modality imaging and analysis is increasingly employed, in which images acquired by different modalities such as (for example) CT and PET are fused, compared side-by-side, or otherwise combined or integrated.

Another type of processing is volume-based processing. However, volumetric image data sets are large, and may be difficult to transmit over existing digital data networks. The proliferation of computer terminals or networked computers has led to the expectation in the medical profession that such image data sets should be ubiquitously available at doctors' personal computers, at the nurses' station monitors, and elsewhere throughout the hospital. However, volume-based processing has shortcomings which prevent realization of such expectations in the medical profession. For example, one method of volume-based processing involves re-sampling and processing stacked slices of image data in any direction to produce rendered views of the image data set as a 3d object. These volume image views ideally allow the user to rapidly obtain a global view of a volumetric image data set. In such processing, the volumetric image data set is treated as samples of a volume, instead of as stacked image slices. To perform volume-based processing on a three-dimensional image data set, the entire volumetric image data set is transmitted from the PACS server to the client device. Thus, the entire volumetric image data set is downloaded across the digital network. This is a substantial problem—volumetric image data sets that contain only a few hundred slices entail downloading of at least 100 MB of data to the image viewer, and the transferred data can readily increase into the gigabyte range for larger volumetric image data sets. These large data transfer loads can be difficult or impossible for the digital data network to accommodate. Because of the enormous size of three-dimensional image data sets, the hospital's digital data transfer network can become a bottleneck that slows or prohibits ubiquitous transfer of three-dimensional datasets.

Moreover, the data transfers are intermittent, and not well distributed. The digital data network must have sufficient bandwidth to accommodate the bulk transfer of the entire volumetric image data set from the PACS system to the client; but thereafter transfer rates for the image analysis are greatly reduced or cease altogether. As a result, the reconstruction of these large volumetric data sets at the client has become a critical bottleneck in using volumetric data sets as diagnostic tools or navigational aids.

Possible solutions entail either providing a designated PACS digital data transfer network, which is not cost-effective; or relying on the existing "general purpose" hospital network to handle PACS data traffic. This latter solution imposes large bandwidth requirements on the hospital network, and can lead to intermittent network slowdowns or stoppages during large volumetric image data set transfers. Network slowdowns or stoppages are of especial concern for hospital networks that are also relied upon to transfer life-critical patient monitoring or instrument control data.

Yet another difficulty is that the processing of large volumetric data sets occurs at the client. The entire image data set is transferred to the client, and the client constructs and navigates the three-dimensional dataset locally. This requires the client to have substantial computational and memory resources. In other words, if (for example) the client is the doctor's or radiologist's personal computer, that computer must have substantial memory and a high-speed processor, in order to locally navigate large volumetric image data sets. This can be an inefficient usage of resources, especially if the only other uses of the doctor's personal computer are word processing, email, or computationally light applications.

In an alternative approach, a PACS server loads the volume image data into its memory, constructs a volumetric image model at the server, and responds to requests from the remote client. In the case of image data sets with less than a few hundred slices, this may be accomplished without lengthy latency, but does require large resources, such as memory, network bandwidth, and computational resources, at the server. For volumetric image data sets of thousands of slices, or for heavily used PACS systems that may be providing volumetric navigation for dozens or more users simultaneously operating on numerous different volumetric image data sets, this centralized approach which relies upon the PACS server to carry the computational load can be costly or impractical.

The following provides new and improved apparatuses and methods which overcome the above-referenced problems and others.

In accordance with one disclosed aspect, an image processing system is disclosed, comprising: a server including a processor and storage configured to store a unitary pyramidal representation of a volumetric image, the unitary pyramidal representation comprising a set of coefficient voxels and having hierarchical levels where each successive level adds information for providing increased spatial resolution, and each coefficient voxel corresponds to a defined three-dimensional spatial region of the volumetric image and to a selected level of the hierarchy; and a network interface configured to convey selected coefficient voxels via a network responsive to a request for imaging data of the volumetric image corresponding to a selected spatial region and to a selected spatial resolution.

In accordance with another disclosed aspect, a method is disclosed for transferring volumetric image data from a server to at least one client, said method comprising: transforming a volumetric image into a hierarchical representation comprising a plurality of coefficients, said hierarchical representation comprising a plurality of levels of essentially non-redundant data, wherein a level of said hierarchical representation comprises transform data sufficient to reconstruct said images at a resolution corresponding to said level; partitioning said coefficients into a plurality of voxels, each voxel comprising "n" coefficients in a horizontal direction, "m" coefficients in a vertical direction, and "p" coefficients in a depth direction; requesting, from a client to a server, transform data in the form of voxels from one or more levels of said hierarchical representation necessary to reconstruct at least a portion of the volumetric image; transferring, from a client to a server, a request for coefficients of at least a portion of the volumetric image; transferring, from said server to said client, at least one voxel in response to said request; and reconstructing, at said client, volumetric views of the volumetric image from said at least one transferred voxel.

In accordance with another disclosed aspect, a image navigation and processing method is disclosed, comprising: identifying a selected three dimensional spatial region and spatial resolution for displaying a volumetric image; querying a server storing the volumetric image as a unitary pyramidal representation partitioned into coefficient voxels corresponding to defined three dimensional spatial regions and spatial resolutions of the volumetric image; responsive to the query, receiving from the server coefficient voxels of the unitary pyramidal representation containing image data sufficient to reconstruct the selected spatial region of the volumetric image at the selected spatial resolution; and based on the received coefficient voxels, reconstructing and displaying an image representative of the selected spatial region of the volumetric image at the selected spatial resolution.

One advantage resides in distribution of image data transfers over time so as to reduce network bandwidth requirements.

Another advantage resides in enabling volumetric image navigation without requiring transfer of the entire volumetric image from a server to a client.

Another advantage resides in more compact image data transfers.

Still further advantages will be apparent to those of ordinary skill in the art upon reading and understanding the following detailed description.

FIGS. 1A and 1B diagrammatically show a server/client based image archiving, navigation, and processing system. FIG. 1A shows selected functional components of the server portion of FIG. 1B.

FIGS. 2A and 2B diagrammatically shows a volumetric image acquired by a slice-based imaging system.

FIGS. 3 and 4 diagrammatically depict sagittal and coronal planes, respectively, of the volumetric image dataset of FIGS. 2A and 2B.

FIG. 5 diagrammatically depicts image decomposition performed by the decomposition processor of FIG. 1A.

FIG. 6 diagrammatically depicts the decomposed volumetric image organized as set of volume partitioned coefficient voxels.

FIG. 7 diagrammatically depicts the LLL octant of the volume partitioned coefficient voxels of FIG. 6.

FIG. 8 diagrammatically depicts one of the server/client pairings of the system of FIG. 1B, including diagrammatic indication of selected functional aspects.

Figure 6:
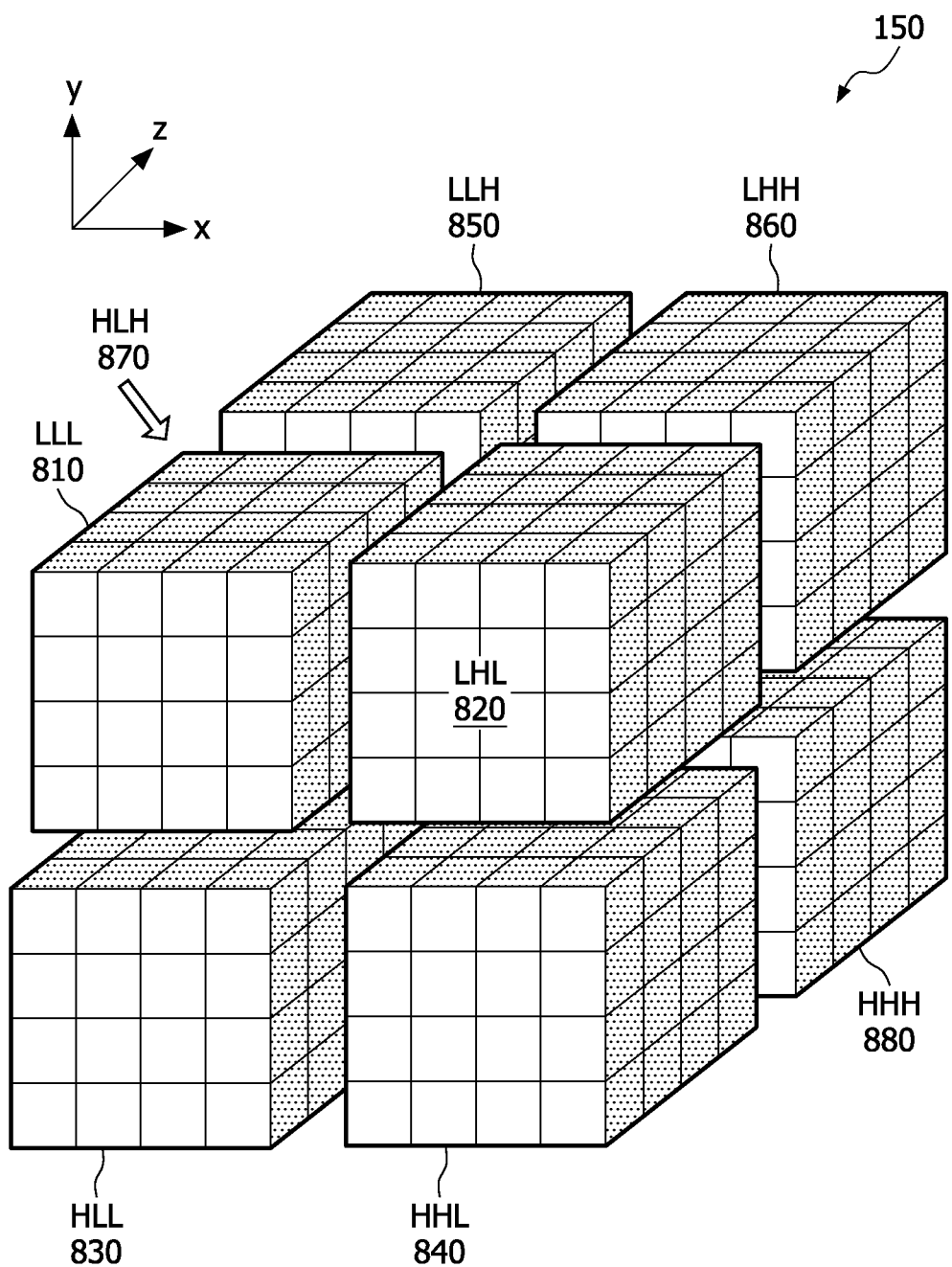

FIGS. 11-16 diagrammatically show identification of voxels in the set of volume partitioned coefficient voxels of FIG. 6, corresponding to various selected spatial regions at various selected spatial resolutions.

Figure 2A:
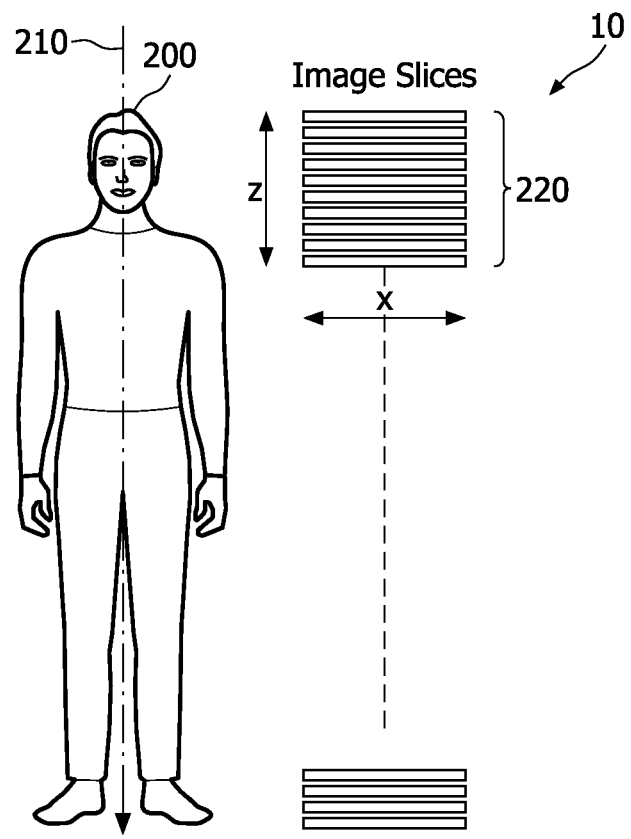
Figure 2B:
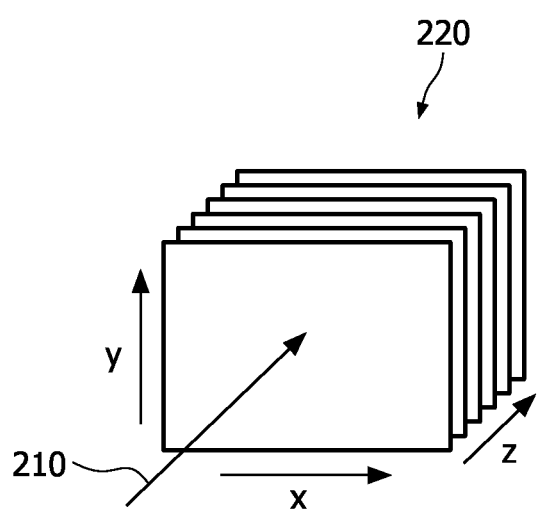

Systems and methods are disclosed herein for processing a source volumetric data set, and in particular, volumetric image data (i.e., three-dimensional image data). With reference to FIGS. 2A and 2B, a source volumetric data set 10 is illustrated as a stack of image slices 220 acquired by a slice-based medical imaging scanner (not illustrated) such as an x-ray, CT, or MR imaging scanner. The source volumetric data set 10 is obtained either directly from the imaging scanner, or may have been previously stored and later retrieved from a suitable database or archive. In illustrative FIG. 2A, a patient 200 is shown lying in a prone position, facing upward. A diagrammatic arrow, labeled 210, drawn through the patient 200, illustrates both an axis and a direction for scanning the patient's body via a medical imaging scanner. A slice-based scanner such as a CT scanner acquires the source volumetric data set 10 as a stack of image slices 220 generated with the orientation depicted by patient 200 along the arrow 210. The stack of image slices 220 collectively define the source volumetric data set 10 extending over the portion of the patient 200 that is scanned by the slice-based scanner.

In some scanner geometries the direction represented by the arrow 210 is referred to conventionally as the axial or z-direction. The image slices 220 are oriented generally transverse to the axial direction of the arrow 210, although some tilt between the slices 220 and the axial direction 210 is contemplated, as for example may be present if a tilted-gantry CT scanner is employed. The image slices 220 are divided into transverse coordinates. In a conventional slice-based scanner geometry notation in which the axial direction is designated as the z-direction, these transverse coordinates are sometimes referred to as the x- and y-directions, and are generally transverse to each other and to the axial direction 210. This conventional geometry is illustrated in FIG. 2B. (Note that in FIG. 2A, the y-direction is oriented transverse to the drawing sheet). As shown in FIG. 2A, the image slices 220 are oriented such that the x-direction is a horizontal direction and the y-direction is a vertical direction. It is to be appreciated, however, that the illustrated (x,y,z) coordinates system is provided as an illustrative example, and other coordinate systems and designations are also contemplated. For example, while FIG. 2A illustrates a left-hand oriented Cartesian coordinate system, a right-hand oriented Cartesian coordinate system is also contemplated, as are various non-Cartesian coordinate systems such as cylindrical or spherical coordinate systems, or another orthogonal coordinate system. Moreover, some imaging sources, such as an MR scanner, may acquire data in a manner other than slices.

A physician, radiologist, or other medical personnel may desire to view different planes or orientations of the source volumetric data set 10 on a display. FIG. 2B illustrates the geometry for an axial plane view or front view of the source volumetric data set 10. More specifically, FIG. 2B illustrates an axial plane view of the image slices 220 on a display. As shown in FIG. 2B, image slices 220 are oriented with reference to the patient 200 with x in a horizontal direction, y in a vertical direction, and z in an axial or depth direction. The x, y, and z dimensions of the image slices 220 of the axial view on a display coincide with the dimensions in the schematic view in FIG. 2A. Image slices 220 are oriented in space such that the front of each slice can be viewed as a user scrolls through the stack of image slices 220 in the z dimension from the front of the stack to the back of the stack. The order of the image slices 220 coincide with the scanned direction as indicated by the arrow 210 in FIG. 2A.

Figure 3:
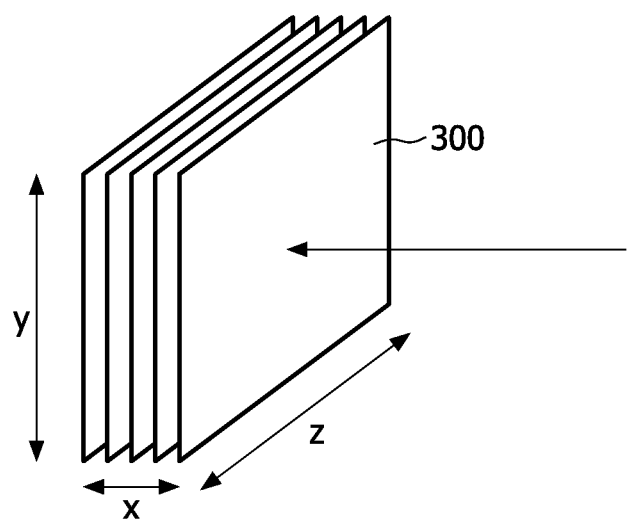
Figure 4:
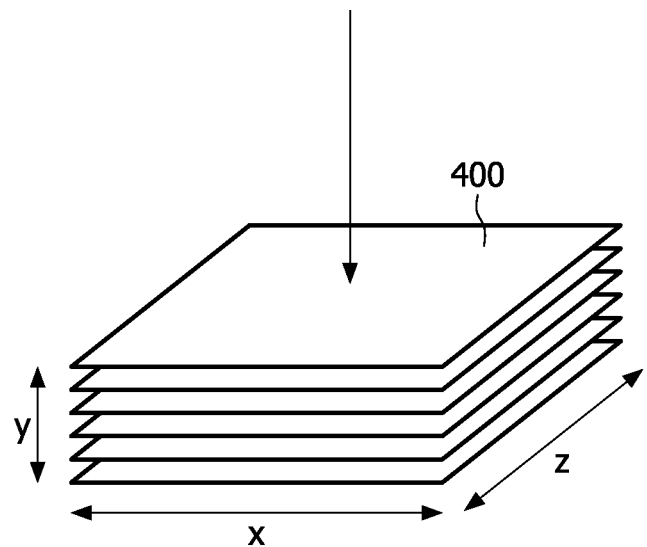

With reference to FIGS. 3 and 4, although the volumetric data set 10 was acquired by scanning at one orientation, a physician, radiologist, or medical personnel may desire to view different planes of the source volumetric data set 10. FIG. 3 illustrates another plane for viewing the volumetric data set. For this view, referred to as a sagittal plane view in the context of the anatomical geometry shown in FIG. 2A, slices of volumetric data are viewed from left to right, relative to the orientation of the original scanned image. FIG. 3 shows the orientation and dimensions of image slices 300 in the saggital plane view respective to the original scanned x, y and z dimensions. For the sagittal plane view, a slice of the image may be viewed on an output display such that the original z dimension of an image slice is viewed horizontally, and the original y dimension of the image slice is viewed vertically. The user may scroll through the stack of image slices in the x dimension.

FIG. 4 illustrates another anatomically interesting plane for viewing source volumetric data set 10. For this example, a coronal plane of image slices are shown. For a coronal plane view, the slices of images 400 are viewed from top to bottom relative to the patient scanning orientation of the FIG. 2A. For coronal plane viewing, the original x dimension of an image slice is viewed horizontally, and the original z dimension of the image slice is viewed vertically. The user may scroll through the stack of image slices in the y dimension.

More generally, any oblique plane (that is, any arbitrary plane other than the axial, sagittal, and coronal anatomical planes illustrated in respective FIGS. 2A, 3, and 4) may be selected for viewing and generated from the volumetric data set 10. For example, an oblique plane may be defined as a plane 30° from the normal plane of the horizontal axis (i.e, 30° from the original plane in which the images were scanned).

Figure 1A:
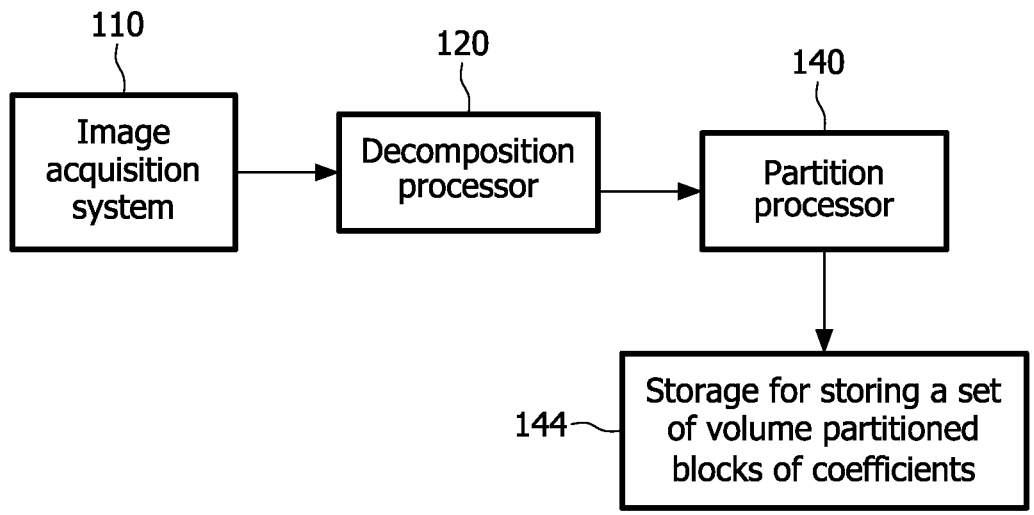
Figure 1B:
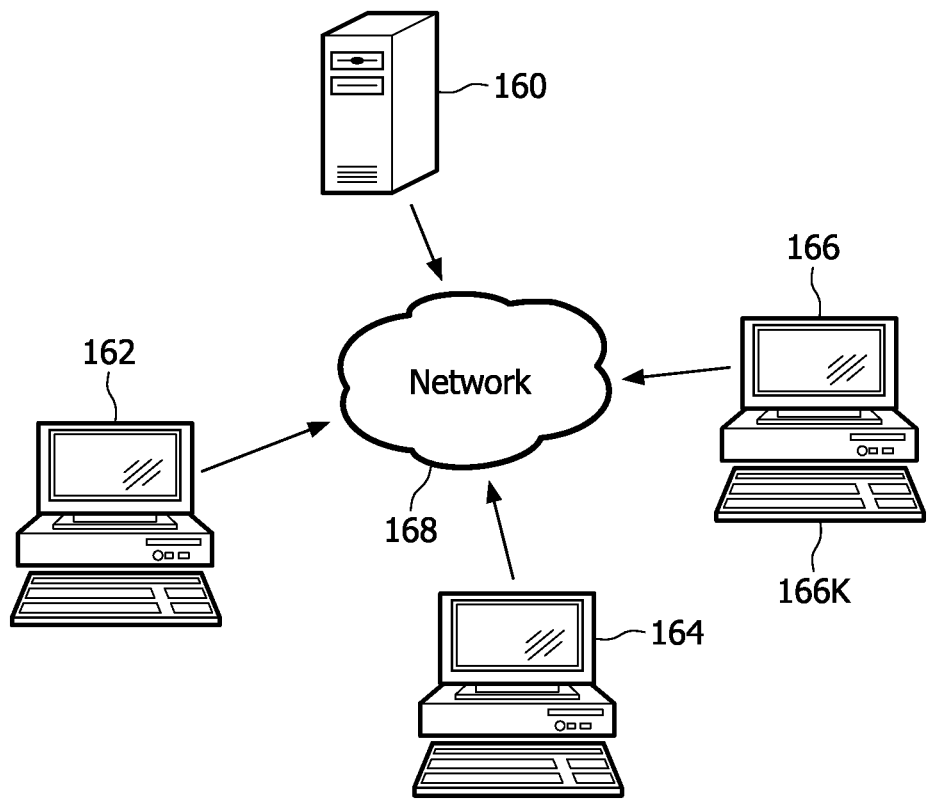

One exemplary system and method for processing a source volumetric data set 10 is shown in the block diagram overviews in FIGS. 1A and 1B. Overall, the source volumetric data set 10 is processed for storage on a server 160 and distribution over network 168 for display on client computers 162, 164, and 166. The client-server relationship is shown in more detail in FIG. 1B. Server 160 and client computers 162, 164, 166 communicate with each other through network interfaces or other communication means for network communication in the server-client architecture.

With continuing reference to FIGS. 1A and 1B, the server 160 includes or embodies a decomposition processor 120 for performing decomposition processing, a partition processor 140 for performing partition processing, and suitable data memory or storage 144 for storage of the volume partitioned coefficients. The storage 144 may comprise, for example, random access memory (RAM); magnetic, optical, or non-volatile solid-state memory; or so forth. The server 160 may embody the processor elements 120, 140 as random access memory (RAM); magnetic, optical, or non-volatile solid-state memory; magnetic, optical, non-volatile solid-state, read-only memory (ROM) or so forth which stores executable code defining the processor elements 120, 140. The server 160 is any suitable digital device or combination of digital devices that is accessible through a network via one or more clients such as illustrated clients 162, 164, 166 employing any suitable server-client or other network architecture. More generally, the clients are contemplated to be any digital device configured to communicate with the server 160 via the network 168 and including a suitable display for displaying images, image portions, image renderings, or the like. The clients include, for example: personal computers; dumb terminals; personal data assistants (PDA's); cellular telephones; other network servers that include display capability; and so forth. The clients 162, 164, 166 may include or embody suitable software for performing volumetric image navigation or other image processing. The network 168 is for example a wired, wireless, or hybrid wired/wireless digital data network, and may more specifically include the Internet, a hospital data network, a dedicated PACS data network, and so forth, or various combinations thereof.

In FIG. 1A, source volumetric data set 10 is acquired by an image acquisition system 110, such as a CT scanner, or is retrieved from a memory, and is processed by a decomposition processor 120 and a partition processor 140. Optionally, quantization and compression processing (not shown) can also be used, as known to those having ordinary skill in the art. Decomposition processing performed by the decomposition processor 120 and partition processing performed by the partition processor 140 (as well as any other optional processing such as quantization and compression processing) are performed either directly on server 160 or on some other computer (not shown) which is accessible by or in communication with server 160.

With returning reference to FIG. 1A, some suitable embodiments of the decomposition processor 120 and the corresponding decomposition processing are described in further detail. In general, "decomposition processing" refers, for example, to the use of a unitary pyramidal transform, such as a wavelet transform, to generate a pyramidal data structure including transform coefficients hierarchically arranged at various levels. For a volume of data such as the source volumetric data set 10, decomposition processing entails the use of a transform to generate a three-dimensional pyramidal data structure 30 including volume transform coefficients at various levels. The transform is for example applied in three transverse or orthogonal dimensions to generate the three-dimensional pyramidal data structure 30 (e.g., see FIG. 5). The volume transform coefficients that are generated from the decomposition processor 120 are invertible to the original source volumetric data set 10. Moreover, the transform coefficients are spatially localized, so that the transform coefficients preserve the data corresponding to a particular area of the image. The transform coefficients at each level of the generated three-dimensional pyramidal data structure 30, together with coefficients from higher (i.e., lower resolution) levels (if any), are sufficient to reconstruct the source volumetric data set 10 at a resolution corresponding to the transform coefficients. The transform coefficients along with coefficient coordinates that identify the coefficients in the three-dimensional pyramidal data structure 30 are hereinafter referred to collectively as transform data in a volume.

The three-dimensional pyramidal data structure 30 is either generated directly on the server 160 or on an associated computer or processor (not shown) which is accessible by or in communication with server 160, or is otherwise capable of sharing the three-dimensional pyramidal data structure 30 with the server 160.

Decomposition processing is achieved by a decomposition processor 120 embodied as software or hardware with executable instructions, or a combination thereof, for generating the three-dimensional pyramidal data structure 30 with volume coefficients. Appropriate hardware and software of a decomposition processor are described more fully in Chang et al., U.S. Pat. No. 6,711,297, which is incorporated herein by reference in its entirety. As an illustrative example, one suitable decomposition transform is a wavelet transform. Wavelet transform processing is a form of sub-band decomposition, which consists of separating high-pass information from low-pass information. In sub-band decomposition, a finite impulse response (FIR) filter is used. Either the same or different FIR filters can be used at each stage of the decomposition process resulting in the three-dimensional pyramidal data structure 30 diagrammatically illustrated in FIG. 5. One suitable family of FIR filters is wavelet filters. One suitable wavelet filter is the floating point 5,7 biorthogonal wavelet kernel (Daubechies) specified and used in the JPEG 2000 standard. Other suitable wavelet filters are, for example, the 5,3 integer wavelet kernel or the 7,9 floating point wavelet kernel as specified in the JPEG 2000 image compression standard. When such a wavelet system and filter, or similar system and filter, are used, the transform is suitably referred to as a wavelet transform.

One advantage of a wavelet (or finite support sub-band) decomposition is that the geometry of the original data set 10 is preserved by the generated transform coefficients. This allows the identification of the sub-set of coefficients required to reconstruct any sub-resolution, or any sub-part of an image. This characteristic is set forth in Chang et al., U.S. Pat. No. 6,711,297 which is incorporated herein by reference in its entirety.

Wavelet transforms can employ various types of kernels to generate three-dimensional pyramidal data structure 30. Fixed point kernels are one suitable type of wavelet transform kernel. The use of fixed point kernels generates fixed point coefficients for the three dimensional pyramidal data structure 30 that allow perfect reconstruction (lossless reconstruction of the original input) without requiring floating point storage.

Another suitable wavelet transform kernel type is the floating point kernel type, which can be used to generate the three-dimensional pyramidal data structure 30 consisting of floating point coefficients. For a given filter length, a wavelet transform with floating point kernels produces higher quality low resolution image data than a transform with fixed point kernels. A wavelet transform, with floating point kernels, is used for improved signal to noise ratios in compression applications. Thus, a wavelet transform, with floating point kernels, enables lossy compression at a high signal to noise ratio (SNR) but at a level that is visually lossless. This approach permits attaining compression ratios for images between 3 and 20 or more to 1, and therefore is suitable for general distribution of images. Use of floating point kernels also generates an aggregated higher percentage of information in the low component of the three dimensional pyramidal data structure, but is not losslessly invertible unless the full floating point resolution of the coefficients is preserved (i.e., stored).

An illustrative decomposition employing a wavelet transform with floating point kernels is suitably defined by the decomposition function $\hat{W}I=C$, where $\hat{W}$ defines the transform function for a transform that utilizes floating point kernels, I represents the source data 10 (that is, the image); and C represents the transformed data (that is, the transformed image).

A multi-resolution format is implicit in the three-dimensional pyramidal data structure 30 because the decomposition processor and corresponding wavelet transform function generates mathematically independent information among the hierarchical levels of the three-dimensional pyramidal data structure 30. Accordingly, there is no redundant information in the three-dimensional pyramidal data structure 30 because the three-dimensional pyramidal data structure 30 contains unique data at each different hierarchical level. The three-dimensional pyramidal data structure 30 is not merely multiple replications of the source data at different resolutions consisting of redundant information. The mathematically independent nature of the wavelet transform minimizes the amount of data transferred over a network by requiring only the transfer of "additional data" corresponding to for example, deeper hierarchical levels (not previously transferred to the client from the server) to construct a given image. For example, as the user zooms in on a particular region during image navigation, only data corresponding to the deeper hierarchical levels providing higher resolution for the zoomed area are transferred a client to implement the zoom operation.

The use of the wavelet transform to generate the three dimensional pyramidal data structure 30 provides a scalable solution for transferring different portions of a large volumetric data file. By "scalable", it is meant that the amount of data required from the server database is directly proportional to the pixels to be displayed at the client. That is, the amount of information required from the server is independent of the size of the entire volume, and only dependent on the requirements for display at the client. For example, if a client only has to display a ¼ resolution (XY) version of an axial image—only those coefficients are requested from the server. When the volumetric source image 10 is decomposed into the three dimensional pyramidal data structure 30, the coefficients representing sub-images and sub-resolution images are extracted directly from the memory of the server 160. The server 160 then transmits only this data, in the form of coefficients, required to reconstruct the exact size of the desired image for display at the client.

The wavelet transform is also lossless, in that no data from the original source data is lost in the decomposition into the hierarchical data representation. Although wavelet transforms are described herein as illustrative examples of the decomposition processing, decomposition processing employing other unitary pyramidal representations are also contemplated.

Figure 5:
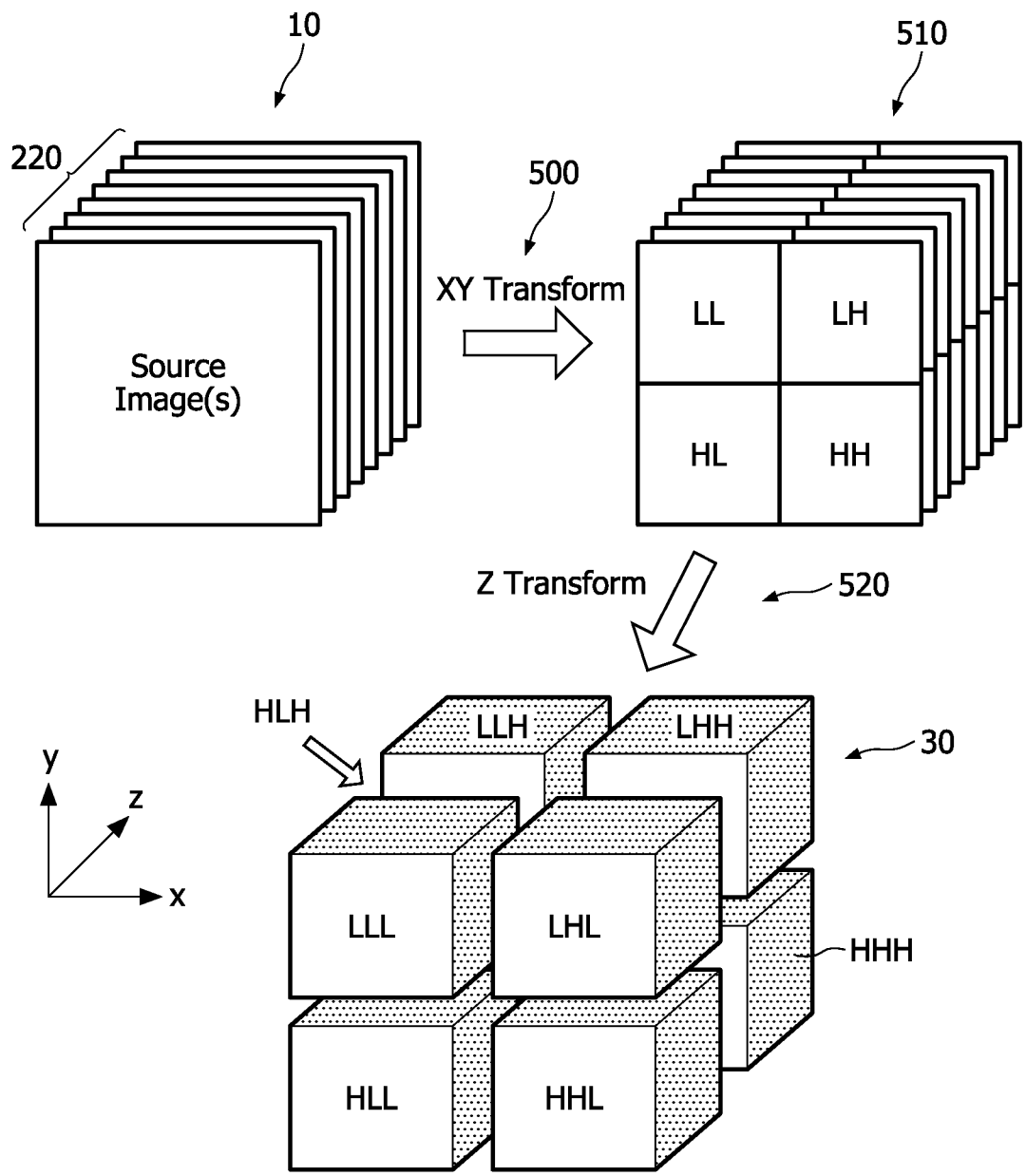

With reference to FIG. 5, for volumetric image navigation applications, it is recognized herein that it is advantageous to perform the transform in three dimensions in order to generate the unitary pyramidal representation 30 with wavelet coefficients along all three spatial directions (e.g., x, y, and z for the illustrative coordinates of the drawings). FIG. 5 illustrates a computational example in which an in-plane wavelet transform 500 is first applied to the individual axial source image slices 220 to generate intermediate data 510, followed by a wavelet transform 520 applied to the intermediate data 510 along the axial or z direction to generate the final three-dimensional pyramidal data structure 30 and volume coefficients. More generally, to generate the three-dimensional pyramidal data structure 30, the same or different transforms 500, 520 are applied across the three transverse or orthogonal spatial directions. The selection of the transforms 500, 520 used by the decomposition processor 120 is dependent upon the particular characteristics of the desired three-dimensional pyramidal data structure 30. To generate the hierarchy, each level of the three dimensional pyramidal data structure 30 is generated by recursive decomposition of the low-pass, "LLL", of the previous higher level. The recursion can be the same transform pattern and kernels, or any different set of transform kernels or pattern. This recursion continues until a level of the three dimensional pyramidal data structure 30 reaches a predetermined size. For example, the lowest level in the three dimensional pyramidal data structure 30 for source volumetric data set 10 having an aspect ratio of one-to-one-to-one consists of a low-pass component of 128×128×128. However, other granularities of resolution may be generated. Moreover, any quadrant may be used in the recursion process with any desired transform. In the approach illustrated in FIG. 5, the acquired axial slices 220 are transformed by the in-plane transform 500 the same number of times in the column and row dimensions (i.e., x and y directions) to maintain the same aspect ratio between the transformed data of the three dimensional pyramidal data structure 30 and the original source volumetric data set 10, while the transform 520 applied in the axial or z direction can be any number of transform levels (zero or more). It should also be noted that the order of transform applications can be different from that shown in FIG. 5—for example, the axial transform 520 can be applied before the in-plane transform 500.

With continuing reference to FIG. 5, as part of the decomposition, information is aggregated into the "low low low" (LLL) quadrant of the decomposition. As one non-limiting example of decomposition, kernels of the wavelet transform can be selected so as to aggregate the maximum amount of information about the original data set into the LLL (low low low) quadrant of the three-dimensional decomposition while maintaining computational efficiency of the transform. This characteristic of wavelet transforms permits transfer, and subsequent display, of a good representation of the source image at a particular resolution while maintaining the computational efficiency of the transform. One of the criteria for selection of wavelet kernel is that the data aggregated in the LLL quadrant of coefficients is a good representation of the complete data set, that is, the reduced resolution set of data represented by the LLL quadrant of coefficients at any hierarchical level is appropriate to use as the display data set for that resolution. Thus, it is possible to directly utilize the LLL transform coefficients quadrant at various levels as pixels. The use of floating point kernels generates an aggregated higher percentage of information in the low component of the three dimensional pyramidal data structure 30, but is not losslessly invertible without preserving the full floating point resolution of the coefficients.

With continuing reference to FIG. 5, the first or in-plane transform 500 performed by the decomposition processor 120 generates, in a first iteration, a one level Mallat (separable) transform structure, corresponding to the intermediate data 510 shown in FIG. 5, for each of the component image slices 220. The low-pass LL quadrant is generated along with high-pass quadrants consisting of the low-high (LH), high-low (HL), and high-high (HH) quadrants of the decomposition 500. The second or axial transform 520 of the decomposition process is applied across the axial or z direction to produce the final three-dimensional pyramidal data structure 30. This second transform along the axial or z-direction again produces low and high pass regions, so that the final three-dimensional structure includes eight octants: LLL; LLH; LHL; LHH; HLL; HLH (not visible in the diagrammatic perspective view of FIG. 5); HHL; and HHH. To perform the recursive decomposition so as to generate hierarchical levels, the LLL octant is used as a new input to the decomposition processing, and the decomposition process can recur to generate one or more additional levels, depending on the size of the input data. A termination condition such as a minimum x, y, z dimension can be used to determine how many levels of decomposition, and in what direction, the transform is to be used.

Notably, the second or axial transform 520 may be omitted. In such a situation, the three-dimensional pyramidal data structure 30 is formed by aggregating information from sequential slices of the data set. The LLL octant and corresponding LHL, HLL and HHL octants are made by aggregating coefficients across the intermediate data 510, and there are no corresponding LLH, LHH, HLH, and HHH octants. Continued transform processing can be applied to the LLL octant of coefficients.

Alternatively, the decomposition processing performed by the decomposition processor 120 may use a wavelet transform with fixed 5,3 integer wavelet kernels as specified in the JPEG 2000 image compression standard, though any integer wavelet kernel preserving low frequency detail efficiently could be used. A characteristic of the use of the fixed point kernel transforms is to preserve a perfect reconstruction representation by having integer coefficients in the representation, as described in U.S. Pat. No. 6,711,297 which is incorporated herein by reference. As a further alternative, a wavelet transform using floating point kernels is employed, and the resultant coefficients are scaled or quantized to provide integer pixel values. In such embodiments, the floating point wavelet kernel comprises the 7,9 floating point wavelet kernel as specified in the JPEG 2000 image compression standard.

A characteristic of wavelet transforms, and sub-band coders in general, is that the transformed data produces the same number of coefficients as there are input samples. This one-to-one correspondence, combined with the characteristics of a geometry preserving transform such as FIRs and compact support wavelets allow computation of the expansion coefficients for reconstructing any volume of interest at any resolution in the original data set. In general, the number of coefficients required to reconstruct N pixels is proportional to N—so the network and computational bandwidth required to transfer and reconstruct the volume of interest is independent of the size of the parent data set, and only dependent on the size of the sub-volume of interest requested at the client Although described in the context of a left-hand Cartesian coordinate system, the decomposition processing performed by the decomposition processor 120 can in general operate in other coordinate systems, such as a right-hand Cartesian coordinate system, a polar coordinate system, a cylindrical coordinate system, or so forth. In the case of a three-dimensional orthogonal coordinate system, it is typically convenient to apply the unitary pyramidal transform along the three coordinate directions of the three-dimensional orthogonal coordinate system so as to generate the three-dimensional pyramidal data structure 30. In the illustrated embodiment, the orthogonal coordinate system is the left-hand Cartesian coordinate system, and the wavelet transforms 500, 520 are applied along the x, y, and z coordinate directions.

Figure 7:
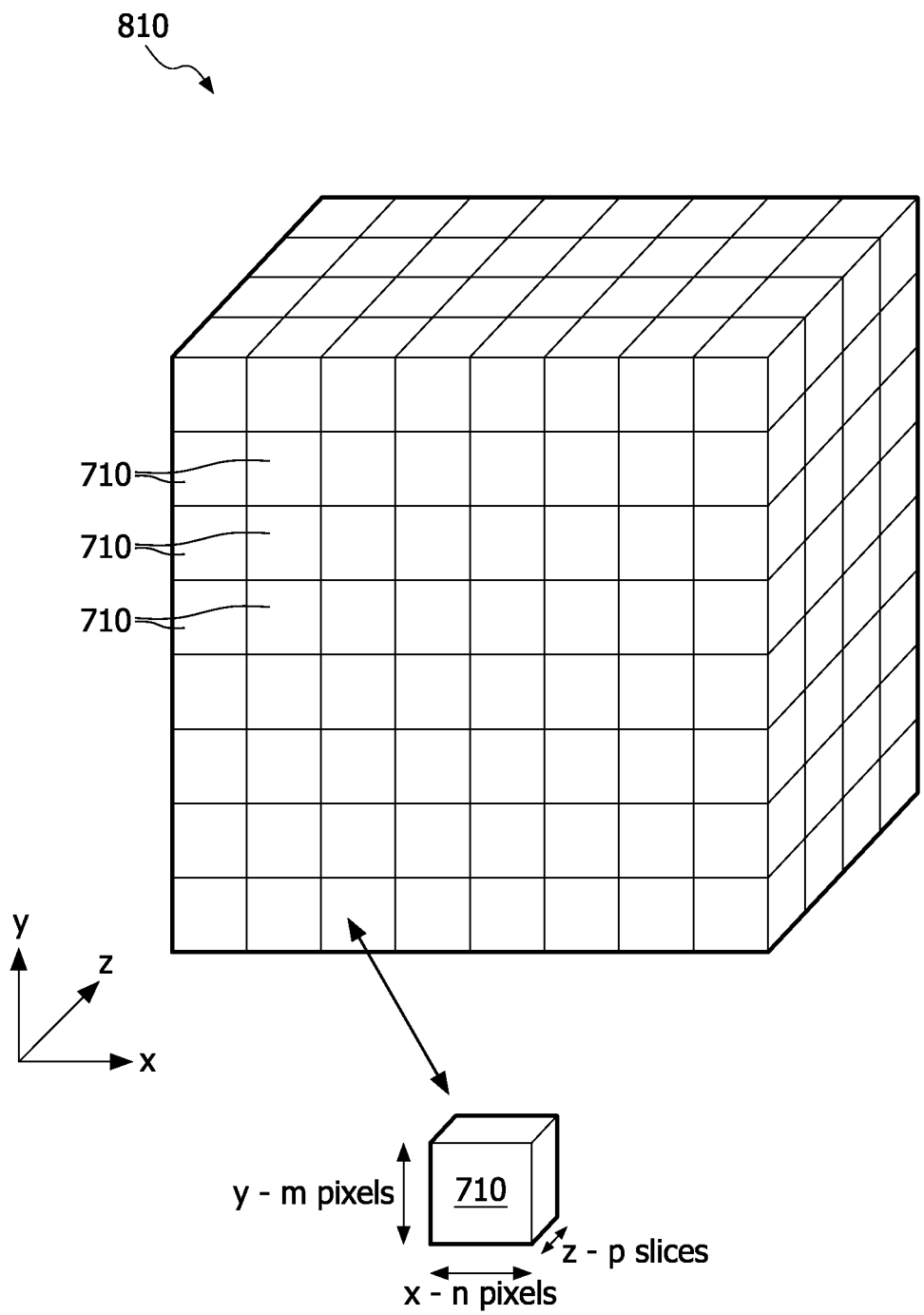

With reference back to FIGS. 1A and 1B and with further reference to FIGS. 6 and 7, the octants of the three-dimensional pyramidal data structure 30 are processed by the partition processor 140 to generate a set of volume partitioned blocks of coefficients 150. Each block of coefficients generated by the partitioning is referred to herein as volume pixel elements, or voxels for short, which are depicted in FIG. 7 as voxels 710. The partitioning of the transform data 30 is suitably performed as described in Huffman, U.S. Pat. No. 6,925,208, which is incorporated herein by reference. However, the partitioning performed by the partition processor 140 is in three dimensions and on all eight octants LLL, LLH, LHL, LHH, HLL, HLH, HHL, HHH, so as to produce three-dimensional voxels 710 each corresponding to a defined three-dimensional spatial extent of the original volumetric image 10.

FIG. 6 depicts the partition of the LLL octant of the three-dimensional pyramidal data structure 30 into a block of voxels 810. Similarly, the LHL octant of the three-dimensional pyramidal data structure 30 is partitioned into a block of voxels 820. The HLL octant of the three-dimensional pyramidal data structure 30 is partitioned into a block of voxels 830. The HHL octant of the three-dimensional pyramidal data structure 30 is partitioned into a block of voxels 840. The LLH octant of the three-dimensional pyramidal data structure 30 is partitioned into a block of voxels 850. The LHH octant of the three-dimensional pyramidal data structure 30 is partitioned into a block of voxels 860. The HLH octant of the three-dimensional pyramidal data structure 30 is partitioned into a block of voxels 870 (not visible in the perspective view of FIG. 7). The HHH octant of the three-dimensional pyramidal data structure 30 is partitioned into a block of voxels 880.

FIG. 7 depicts the block of voxels 810 corresponding to the partition of the LLL octant of the three-dimensional pyramidal data structure 30. Individual voxels are indicated by reference number 710. Each voxel 710 includes coefficients that correspond to an n×m×p block of spatial pixels of the original volumetric image 10. In the illustrated embodiments, the dimension "n" is along the horizontal or x-direction, the dimension "m" is along the vertical or y-direction, and the dimension "p" is along the axial or depth or z-direction. For example, one voxel 710 may comprise the coefficients that map to 4×4×4 block of pixels of the volumetric image. That is, in such an embodiment n=m=p=4. In another illustrative embodiment, one voxel 710 may comprise the coefficients that map to 8×8×8 block of pixels of the volumetric image, that is, n=m=p=8. More generally, the dimensions n, m, p of the voxel 710 can be different, for example a 8×8×4 voxel is contemplated, wherein n=m=8 and p=4. In general, the three-dimensional pyramidal data structure 30 may be partitioned into any sized voxels 710. Still further, different hierarchical levels of the volume partitioned coefficients may comprise different sized voxels.

FIG. 6 depicts the partitioning of one level of the three-dimensional pyramidal data structure 30, while FIG. 7 depicts the partitioning of one octant (namely the partitioning of the LLL octant). A complete labeling or identification of a single voxel of the set of volume partitioned coefficients 150 is suitably given by the set of coordinates (<level>, <octant>, <x>, <y>, <z>), where <level> identifies the hierarchical level of the voxel in the three-dimensional pyramidal data structure 30 (corresponds to the spatial resolution information provided by the voxel), <octant> identifies the octant (i.e., LLL, LLH, LHL, LHH, HLL, HLH, HHL, or HHH as illustrated in FIG. 5 for the three-dimensional pyramidal data structure 30), and <x>, <y>, and <z> are spatial coordinates of the voxel. Thus, for example, the voxel (2,LLL,<x>,<y>,<z>) represents the voxel corresponding to a spatial region denoted by the spatial coordinates <x>, <y>, <z>, for hierarchical level 2, octant LLL. The set of coordinates (<level>, <octant>, <x>, <y>, <z>) is illustrative, and other arrangements of coordinates and coordinate value conventions can be utilized.

The partition processor 140 optionally performs compression on the voxels 710 to facilitate efficient transfer of image data from the server 160 to the clients 162, 164, 166. Substantially any type of data compression can be employed; it is also contemplated to employ no data compression of the coefficients of the voxels. In one suitable compression technique, the coefficients of each voxel are quantized by a floating point value. The result is truncated towards zero and stored as an integer. Generally, this operation may be expressed as $\hat{Q}\hat{W}I = \hat{Q}R$, where $R = \hat{W}I$ represents a block of coefficients making up a voxel, and $\hat{Q}$ represents the quantization function. For this expression, if truncation toward zero is used, the quantization function $\hat{Q}$ may be expressed as follows:

$$R_Q = \frac{R + .5Q}{Q} \text{ if } R > 0;$$

and $$R_Q = \frac{R - .5Q}{Q} \text{ otherwise,}$$

where Q is a floating point value and the result is consistently truncated (i.e., either towards or away from zero), such that $R_Q$ is a multiple of the quantization bin width Q. The quantization bin widths Q can be different for different hierarchical levels, or for different octants, or most generally for different voxels. A lossless coder such as a Rice encoding function or a Huffman encoding function can be applied to the quantized coefficients $R_Q$ of a voxel in order to compress the coefficients making up the voxel. The output of the partition processor 140 is the set of voxels, each indexed by the set of coordinates (<level>, <octant>, <x>, <y>, <z>) and each compressed for efficient transmission. It should be noted that the set of coefficient voxels making up the volume partitioned coefficients 150 can cover a spatial volume larger than the volumetric image data set 10 (for example, "edge" coefficient voxels may extend beyond the spatial volume of the original image 10), but each pixel in the volumetric data set 10 is resident in (that is, represented by) a unique coefficient voxel.

The above compression employing quantization is a lossy compression, since the "residual" information caused by the quantization is lost. However, if this residual information is sufficiently small, the resulting image may be "visually lossless", meaning that the lost information is not visually perceptible. Optionally, the residual information can be computed, for example by subtracting the actual image from the visually lossless image reconstructed from the compressed coefficients, and stored at the server 160 so as to enable the completely lossless image to be regenerated. In other approaches, lossless compression is employed to compress the coefficient voxels.

Figure 8:
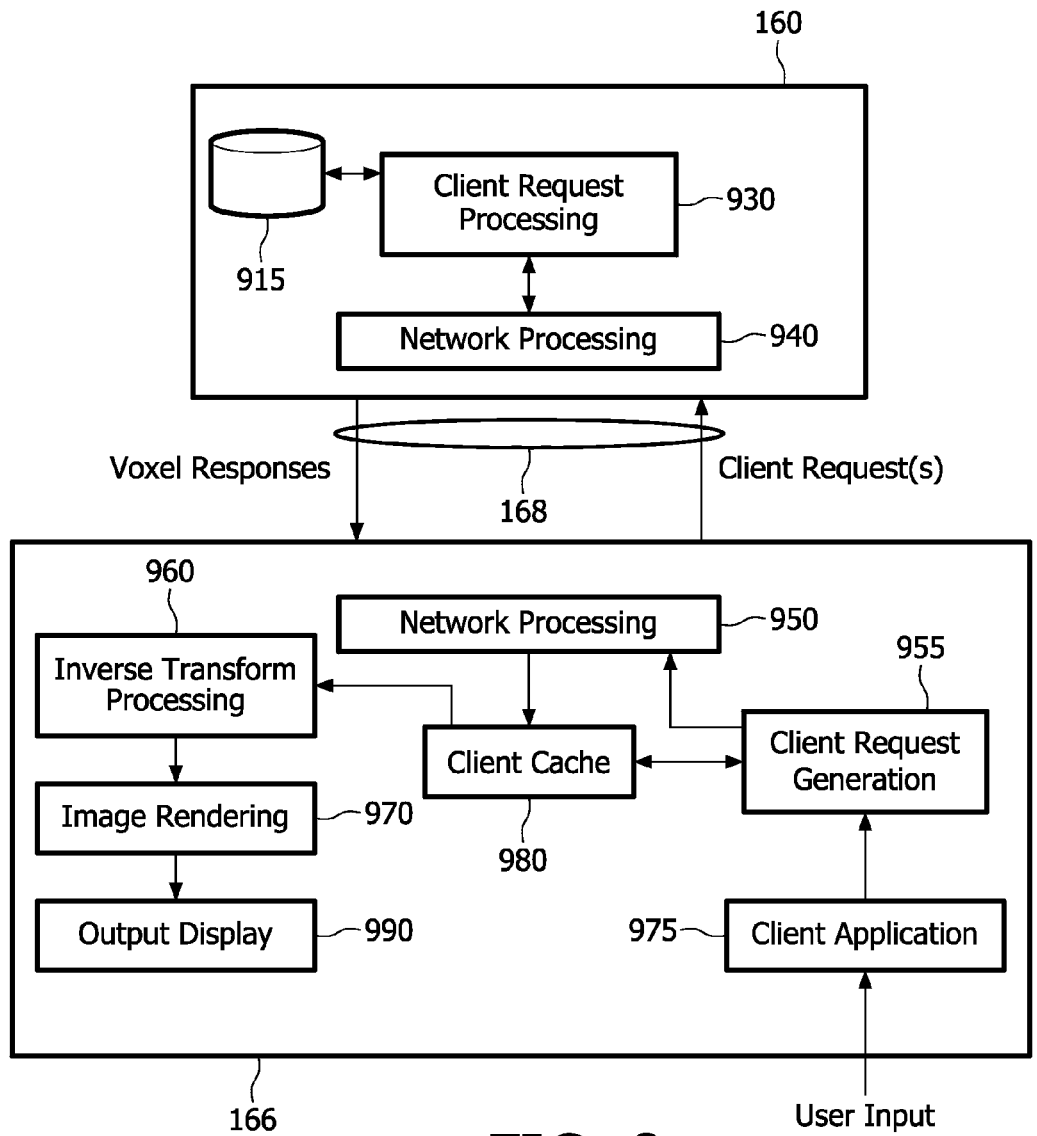

With reference to FIG. 8, an illustrative arrangement by which representative client 166 interacts with the server 160 is described. Typically, an enterprise environment such as a hospital or other medical facility includes at least one server 160 and multiple clients 162, 164, 166, as shown in FIG. 1B, but the example illustrated in FIG. 8 focuses on the single client 166. The client 166 transmits requests to server 160 for portions of the volumetric data set 10, which are stored as the set of volume-partitioned coefficients 150 (that is, coefficient voxels) in a suitable storage medium 915, possibly along with a large number of other volumetric images that are also stored in the server 160. In response to the client requests, the server 160 transfers one or more coefficient voxels that correspond to the requested portions of the volumetric data set 10. In order to generate requests for portions of a volumetric data set 10, the client 166 includes or embodies a client request generation module 955 and client application 975. The client application 975 is, for example, an image navigation and processing application program running on the client computer 166. During initialization for viewing of a specific volume data set, the server 160 sends parameters describing the set of voxel-partitioned coefficients 150, such as spatial dimensions of the image and particulars of the transform structure (e.g., wavelet transform parameters, partition spatial and hierarchy level dimensions, data compression algorithm parameters, and so forth). The client application 975 specifies portions of the volumetric source image for viewing at the client. For example, the client application 975 may comprise a user interface for a medical imaging application that identifies portions of medical images based on input selections from a user. The input selections may be received from the user via any suitable user input device, such as a keyboard, mouse, trackball, trackpad, touch-sensitive screen, or so forth. FIG. 1B depicts an illustrative keyboard 166k as an input device for the client computer 166. The client application 975 may specify three-dimensional pixel coordinates, which define an image block or slice, and resolution of a volumetric source image. Alternatively, the resolution may be computed based on the spatial dimensions of the defined image block or slice together with a priori knowledge of the display resolution of the display device of the client computer 166. The client request generation module 955 maps the pixel coordinates to coefficient coordinates in the three-dimensionally partitioned three-dimensional pyramidal structure. A client-side network processing interface 950 formats the client request for transmission to the server 160 via the digital network 168.

At the server 160, the client request is processed by client request processing module 930 (suitably embodied, for example, as the processor and/or memory of the server 160 executing suitable software). A network processing interface 940 facilitates communication with the network 168. One or more coefficient voxels are identified by the client request processing module 930 as relevant for reconstructing the volumetric data set at the specified resolution. The identified voxels are extracted from the set of voxel-partitioned coefficients 150 stored on or in the permanent storage medium 915, and the data is formatted for the appropriate network transmission protocol. The voxels are transmitted to the client 166 and stored in a client cache 980, and the received and cached voxels are extracted from the network protocol format (and decompressed as necessary if stored at the server 160 in a compressed format). The received and decompressed coefficients are processed by an inverse transform processing module 960 to generate a new or updated image for display. In general, the inverse transform processor 960 executes the inverse of the transform or transforms 500, 520 (see FIG. 5) used to generate the three-dimensional pyramidal data structure 30, and by said inverse operation regenerates the image pixels (or a visually lossless equivalent thereof in the case of lossy compression) for the desired image or image portion within the volumetric data set 10. An image rendering module 970 renders a human-perceptible view from the pixels for display on output display 990 of the client 166.

The client request generation module 955 in some cases generates and sends to the server 160 a client request identifying the selected spatial region and the selected spatial resolution, from which the server 160 determines the requisite coefficient voxels to send back to the client 166. In other cases, the client request generation module 955 identifies the coefficient voxels corresponding to the selected spatial region and the selected spatial resolution at the client end, and conveys to the server 160 the identification of the requisite coefficient voxels. In some of the latter cases, the client request generation module 955 may first query the cache 980 to determine whether the voxels required for rendering are already stored in the cache 980, so as to avoid duplicative retransmitting of those coefficient voxels from the server 160. In some of the former cases, the server 160 may keep track of which coefficient voxels it has sent to a given client, and based on this information may avoid duplicative retransmission of coefficient voxels that should already in the client cache 980.

Figure 9:
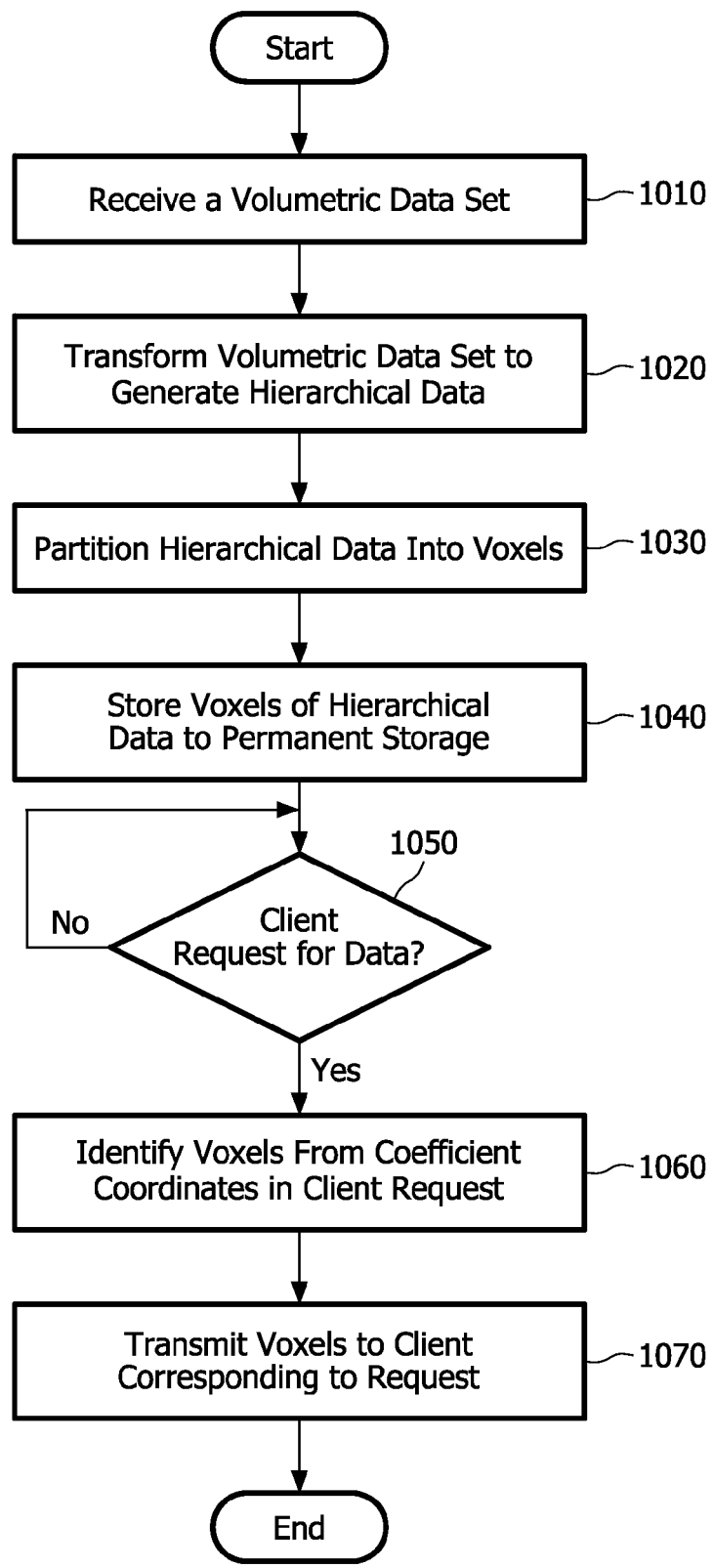
FIG. 9 shows a flow chart of processing performed by the server of FIGS. 1B and 8.

With reference to FIG. 9, a flow diagram illustrates one embodiment for a server process to distribute three-dimensional images. Server 160 receives or stores the volumetric data set 10 for processing in block 1010 of the flow diagram. The volumetric source data set 10 is transformed by the decomposition processor 120 to generate the three-dimensional pyramidal data structure 30 in processing block 1020. The three-dimensional hierarchical data structure 30 is partitioned into a plurality of voxels, and optionally the coefficients of each voxel are compressed, in processing block 1030. The partitioned and optionally compressed coefficient voxels are stored in the permanent storage medium 915 at the server 160 in processing block 1040. The server 160 continuously listens for requests for coefficients from a client as long as it does not receive requests for coefficients (see "No" decision as part of the decision block 1050). When the server 160 receives a request for coefficients in processing block 1050 (see the "Yes" decision as part of decision block 1050), the server 160 identifies the requisite voxels from the coefficient coordinates specified in the client request in processing block 1060. The identified voxels are then transferred to the client in response to the client request in block 1070.

Figure 10:
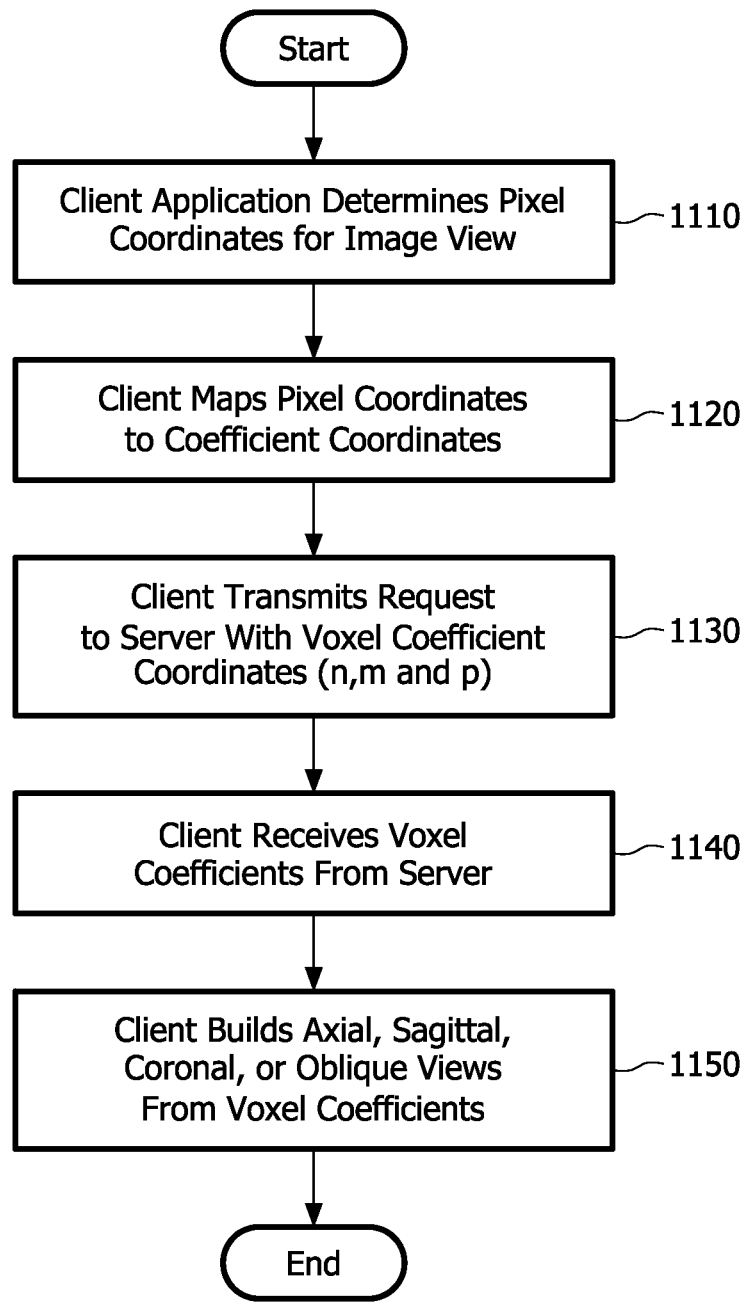
FIG. 10 shows a flow chart of processing performed by a selected client of FIGS. 1B and 8.

With reference to FIG. 10, a flow diagram illustrates one embodiment for a client process of three-dimensional image distribution. The client application 975 running at the client has requirements to display an image. For example, the client application may comprise a medical imaging application for display of medical images at various resolutions. The client application 975 determines the three-dimensional pixel coordinates for an image view of the volumetric source image in processing block 1110. Using the pixel coordinates and resolution, the client maps the pixel coordinates to coefficient coordinates of the three-dimensional pyramidal data structure in processing block 1120. The client formulates a request, with the coefficient coordinates, and transmits the request to the server 160 in processing block 1130. In response to the request, the client receives, from the server 160, one or more coefficient voxels that contain or correspond to the coefficient coordinates specified in the request at block 1140. The client builds one or more volumetric views of the source image with the voxels in processing block 1150. For example, after converting the voxel coefficients to pixels, the client may build an axial, sagittal, coronal, or oblique view from the voxel coefficients. These views can be at any resolution and of any part of the parent volumetric data set 10, where the resolution is controlled by the hierarchical level or levels <level> of the received voxels and the part of the parent volumetric data set 10 available for reconstruction is controlled by the spatial coordinates <x>, <y>, <z> of the received voxels.

If the client application 975 specifies new pixel coordinates and resolution for a new image view, then the client determines which, if any, new coefficient coordinates are required to render the new image view. If the new coefficient coordinates are already cached at the client cache 980, then the client application renders the new view with the cached voxels. On the other hand, if the client does not have all the coefficients required for the new view in cache 980, then the client generates and sends a new request for the new coefficients, the server then transmits those voxels to the client for processing and display.

With reference to FIGS. 11-16, several examples of the selection of coefficient voxels sufficient to reconstruct a selected portion of the volumetric image at a selected spatial resolution are illustrated. The examples of FIGS. 11-16 employ the set of volume-partitioned coefficient voxels 150 diagrammatically depicted in FIG. 6. Each of FIGS. 11-16 shows volume partitioned coefficient voxels at one illustrative hierarchical level having a corresponding hierarchical level resolution. Because of the non-redundant hierarchical arrangement of the unitary pyramidal representation, if the depicted hierarchical level is not the topmost (lowest resolution) hierarchical level, then (although not depicted) it is to be understood that the coefficient voxels for the selected spatial plane or region in the hierarchical levels that are "above" or at lower resolution in the unitary pyramidal representation than the depicted level are also required to reconstruct the image at the selected higher resolution.

Figure 11:
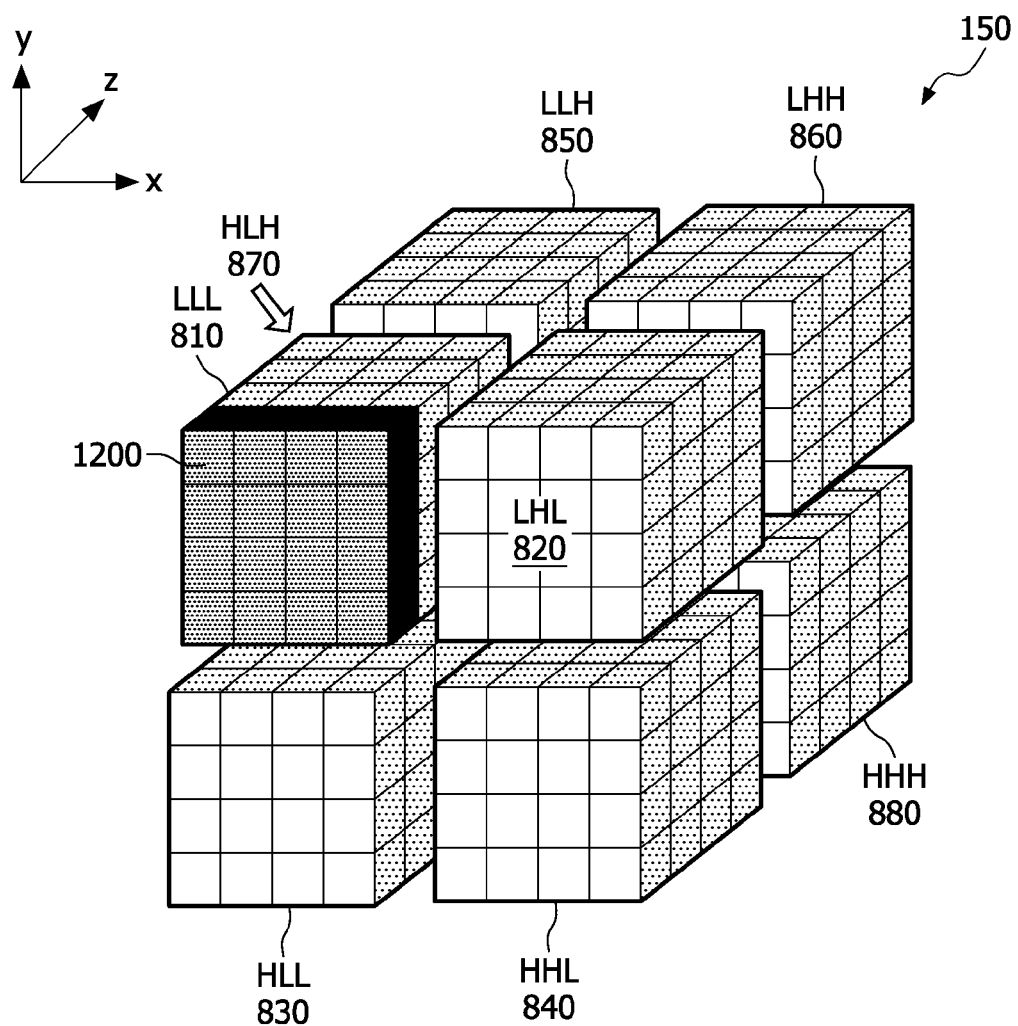
Figure 12:
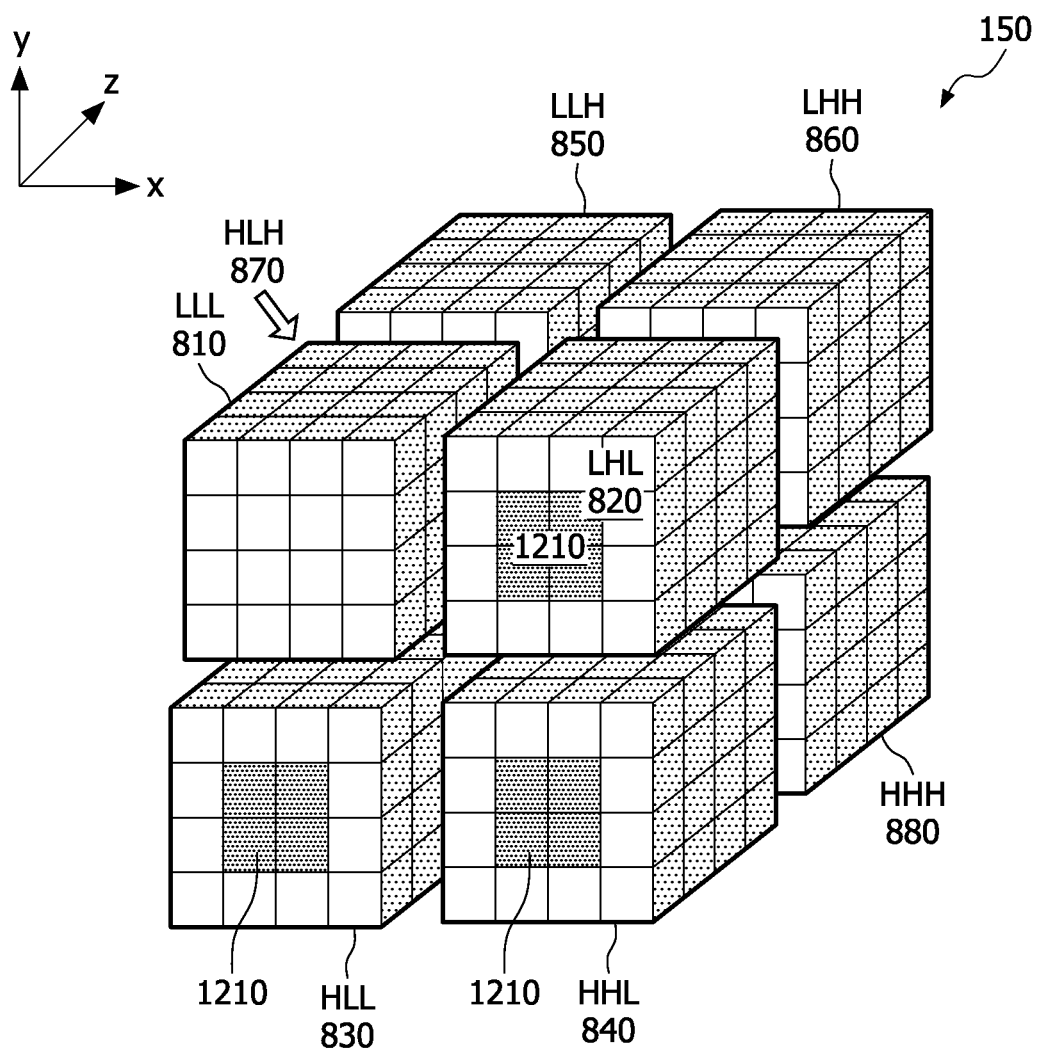

FIGS. 11 and 12 diagrammatically illustrate a "zoom" operation. FIG. 11 identifies coefficient voxels 1200 required to reconstruct an axial view at one-quarter of the full hierarchical level resolution in the x-y (axial) plane and at one-half of the full hierarchical level resolution along the axial or z-direction. The coefficient voxels 1200 are an x-y plane of voxels in the LLL octant of the set of volume-partitioned coefficient voxels 150. FIG. 12 identifies additional coefficient voxels 1210 required to reconstruct a "zoomed" axial view of the same axial plane as FIG. 11, with the same resolution in the axial or z-direction but at higher resolution in the x-y plane. The spatial extent of the zoomed region is smaller, so the additional coefficient voxels 1210 do not span the entire axial (x-y) plane in the coefficient voxels space, but rather have a reduced (x-y) span corresponding to the reduced or zoomed field of view. Note that for the zoomed view, the outermost voxels of the set of coefficient voxels 1200 of FIG. 11 are no longer needed, but optionally remain in the cache 980 for later use if, for example, the doctor or radiologist elects to "zoom out" to a larger field of view.

Advantageously, only the coefficient voxels 1200, 1210 need to be transferred from the server 160 to the client 166 in order to effectuate the axial slice display including the zoom operation. The entire set of volume-partitioned coefficient voxels 150 does not need to be transferred. A further advantage is that transmission of the coefficient voxels is distributed over the navigation session, that is, the first block of coefficient voxels 1200 is transmitted as a group and viewed by the doctor or radiologist, followed later by transmission of the coefficient voxels 1210 that provide the additional image data to effectuate the zoom. In a typical image navigation session in which the doctor successively zooms to higher and higher resolutions focused on a particular region (for example, a region containing a low contrast representation of a lesion or tumor of concern), the transfer of coefficient voxels is still better distributed, with each successive zoom operation typically entailing transfer of a small portion of the requisite voxels since the remainder are already cached at the client due to previous (lower resolution) image viewings.

Figure 13:
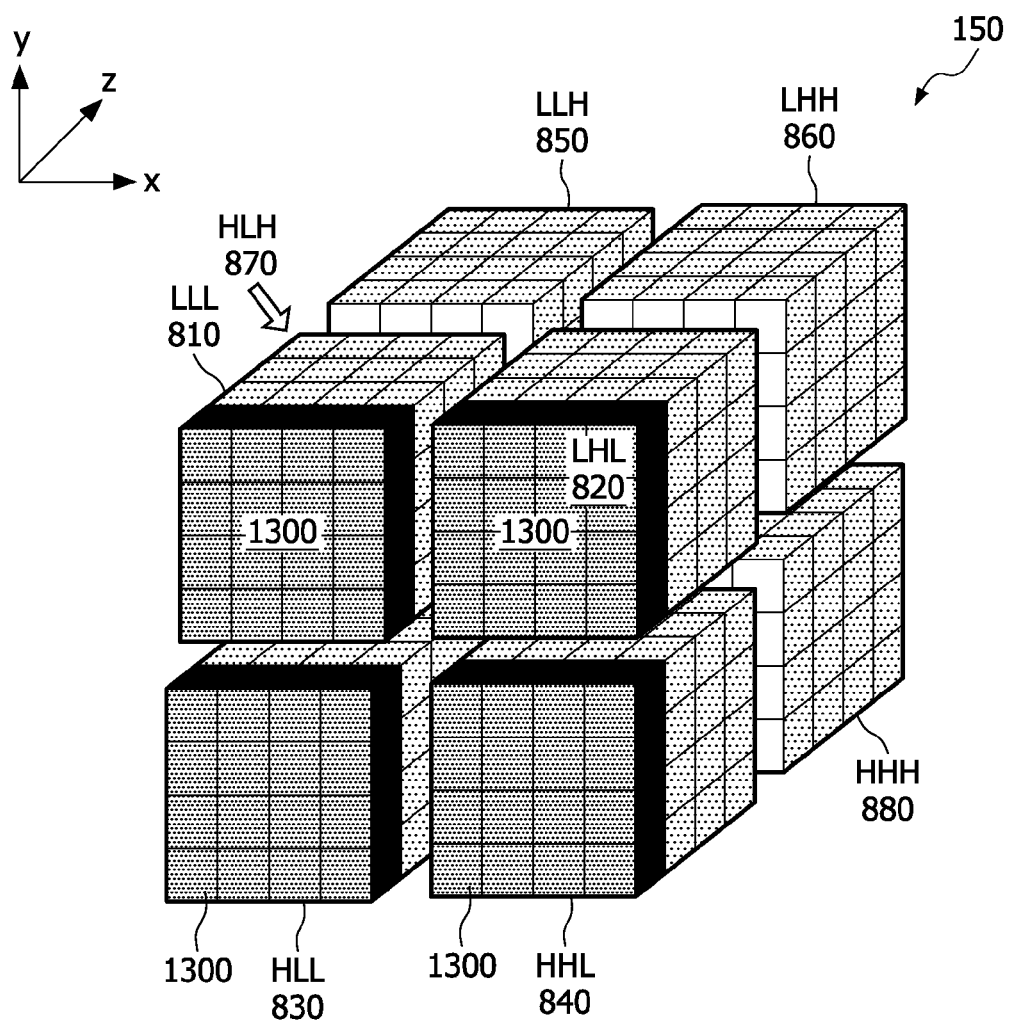
Figure 14:
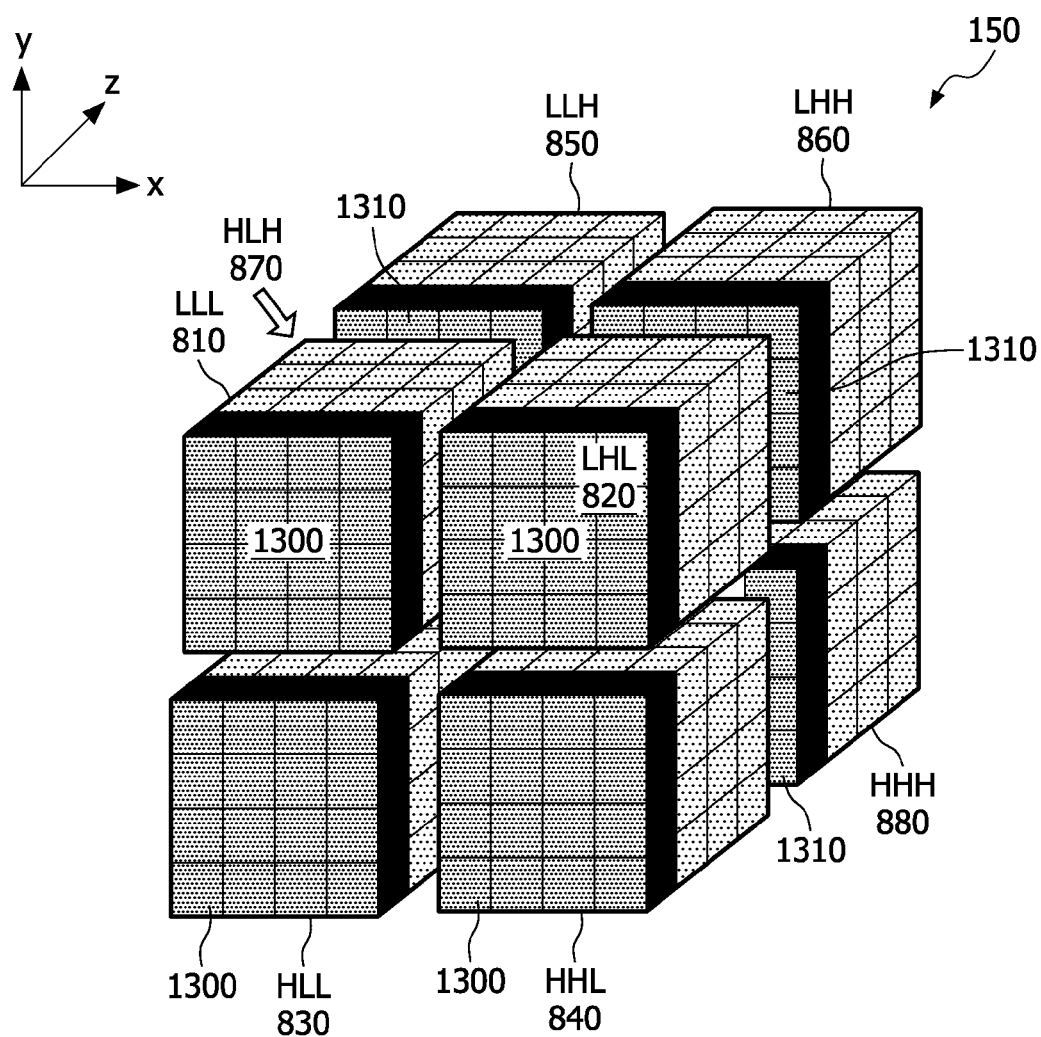

FIGS. 13 and 14 illustrate another example, in which the zooming is performed in the axial or z-direction. FIG. 13 identifies coefficient voxels 1300 required to reconstruct an axial view at full hierarchical level resolution in the x-y (axial) plane and at one-half of the hierarchical level resolution along the axial or z-direction. The coefficient voxels 1300 are an x-y plane of voxels in the LLL, LHL, HLL, and HHL octants of the set of volume-partitioned coefficient voxels 150. FIG. 14 illustrates the coefficient voxels 1300 along with additional coefficient voxels 1310 required to reconstruct the axial view of FIG. 13 with full hierarchical level resolution in both the x-y (axial) plane and at full hierarchical level resolution along the axial or z-direction. The requisite additional coefficient voxels 1310 are the same x-y plane of voxels for the group 1300, but in the LLH, LHH, HLH, and HHH octants. Again, the transferred voxels are a small subset of the entire set of volume-partitioned coefficient voxels 150, and the transmission of the voxels 1300, 1310 is distributed across the image navigation session.

Because the set of volume-partitioned coefficient voxels 150 is three-dimensional in nature, the doctor or other user is not limited in the direction or orientation of viewing, zooming, or panning.

Figure 15:
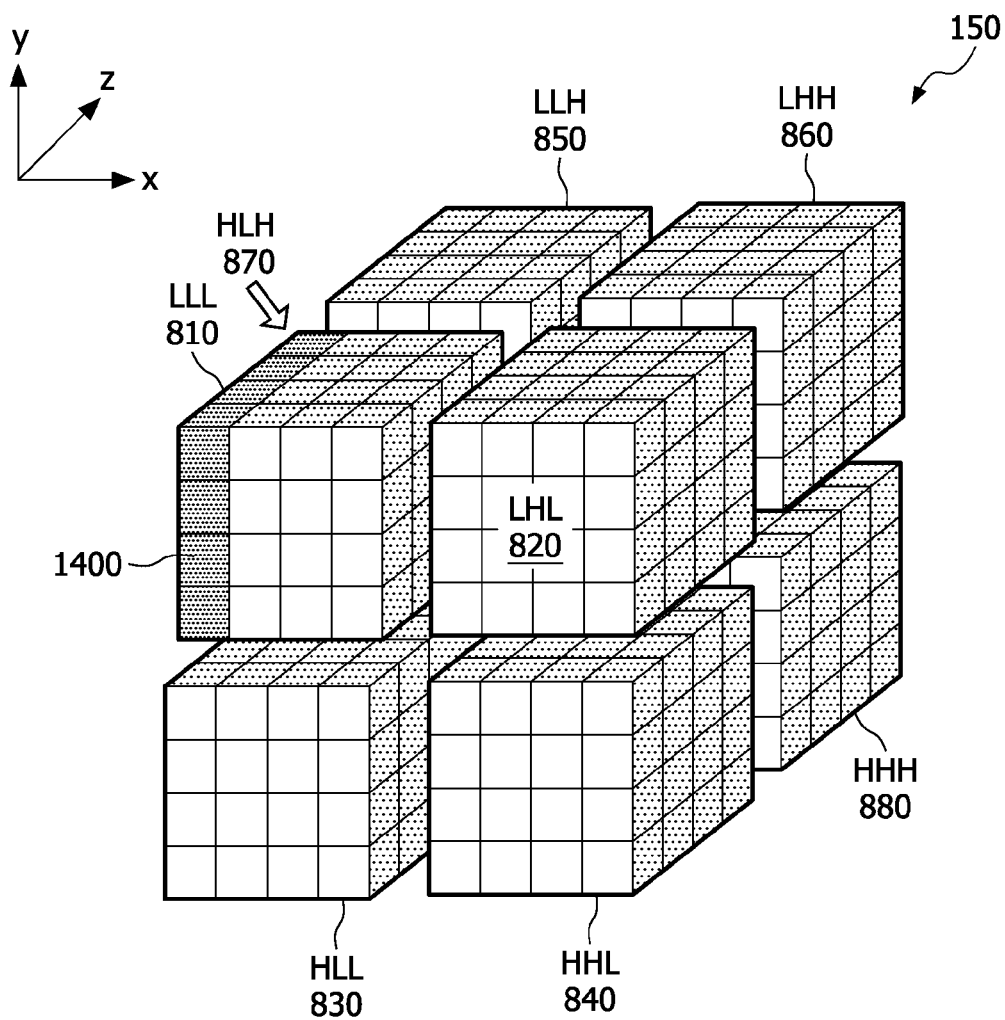

For example, FIG. 15 identifies coefficient voxels 1400 required to reconstruct a sagittal view at one-quarter of the hierarchical level resolution in the sagittal (y-z) plane and at one-half of the hierarchical level resolution along the x-direction. The coefficient voxels 1400 are a y-z plane of voxels in the LLL octant of the set of volume-partitioned coefficient voxels 150.

Figure 16:
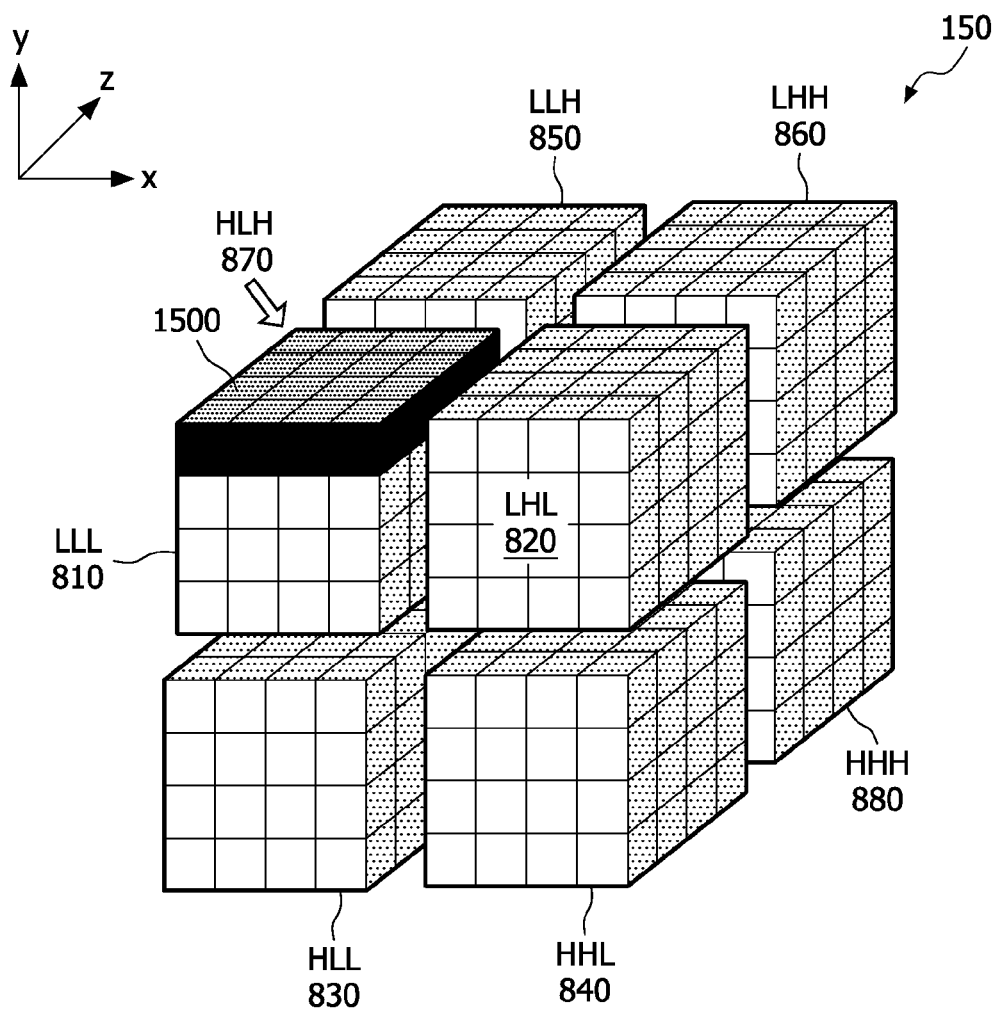

Similarly, FIG. 16 identifies coefficient voxels 1500 required to reconstruct a coronal view at one-quarter of the hierarchical level resolution in the coronal (x-z) plane and at one-half of the hierarchical level resolution along the y-direction. The coefficient voxels 1500 are a x-z plane of voxels in the LLL octant of the set of volume-partitioned coefficient voxels 150.

Although not depicted, zooming operations can be performed in the sagittal or coronal plane analogously to the axial plane zooming operations depicted in FIGS. 11-12 and 13-14. Similarly, zooming operations can be performed on oblique planes by suitable selection and server-to-client transfer of coefficient voxels containing the coefficients corresponding to the spatial image pixels of the oblique plane. Panning operations are also not depicted, but again entail transferring the coefficient voxels corresponding to the additional spatial volume added to the field of view by the panning operation, and discarding (or leaving in the cache) any voxels covering spatial volume that is removed from the field of view by the panning operation.

The illustrated coefficient voxels correspond to contiguous three-dimensional blocks or regions of space. In some applications, the volumetric image may also have a time dimension. For example, a cinematic or "CINE" view may comprise a temporal series of volumetric images of a subject. It is contemplated to incorporate the time dimension into the voxel representation as a fourth dimension, by further applying the unitary pyramidal transform along the time dimension and partitioning along the time dimension to define "four-dimensional" voxels. Each such four-dimensional voxel can be suitably designated by coordinates (<level>, <orthant>, <x>, <y>, <z>, <t>), where <level> identifies the hierarchical level of the voxel in the four-dimensional pyramidal data structure (corresponds to the spatial and temporal resolution information provided by the voxel), <orthant> identifies the orthant (there are now sixteen orthants, i.e., $LLLT_L$, $LLHT_L$, $LHLT_L$, $LHHT_L$, $HLLT_L$, $HLHT_L$, $HHLT_L$, $HHHT_L$, $LLLT_H$, $LLHT_H$, $LHLT_H$, $LHHT_H$, $HLLT_H$, $HLHT_H$, $HHLT_H$, $HHHT_H$ where $T_L$ and $T_H$ designate the division imposed by the unitary pyramidal transform applied along the time dimension), <x>, <y>, and <z> are spatial coordinates and <t> is the time coordinate. Using suitable video navigation and processing software the client can analogously zoom in both space and time, with the server transferring only those four-dimensional coefficient voxels sufficient to reconstruct the spatial and temporal region of the CINE data at the desired spatial and temporal resolution.

To summarize, various embodiments of systems and methods are disclosed herein for processing a source volumetric data set, and in particular, volumetric image data (i.e., three-dimensional image data), in which image data are transformed to a unitary pyramidal representation having hierarchical levels each successive level of which adds information providing increased resolution, and providing spatially localized image information. Suitable unitary pyramidal representations include, for example, wavelet representations such as are disclosed for example in Chang et al., U.S. Pat. No. 6,711,297 which is incorporated herein by reference in its entirety. The systems and methods disclosed herein further partition the transformed unitary pyramidal representation, using techniques disclosed for example in Huffman, U.S. Pat. No. 6,925,208 which is incorporated herein by reference in its entirety.

The systems and methods disclosed herein extend these techniques based on the recognition that by (i) performing the transformation to the unitary pyramidal representation in three-dimensions, and (ii) also performing the partitioning in three dimensions, one can generate a voxel-based unitary pyramidal representation having hierarchical levels each successive level of which adds essentially non-redundant information providing increased resolution, in which the information is also grouped into coefficient voxels each representative of coefficients of a defined three-dimensional block of pixels of the original volumetric image data. Accordingly, this data representation enables rapid conveyance of sufficient data to enable three-dimensional navigation of the volumetric image without entailing bulk transfer of the entire volumetric image data set. A volumetric model can be constructed and the PACS or other image database queried based on the volume and resolution to be displayed at any given time, and the PACS or other image database conveys only sufficient information to render or display that requested volume at the requested resolution.

This disclosed approach reduces the total amount of data to be transferred, and also distributes the data transfer over time in the case of a typical sequence of volume-based navigation. For example, in an initial view used to provide anatomical orientation, the system can convey the entire image but only at the highest hierarchical level or levels of the unitary pyramidal representation corresponding to a low resolution. As the physician "zooms in" on a feature or region of interest, the system conveys only those coefficient voxels of the unitary pyramidal representation corresponding to the enhanced resolution and reduced volume of interest of the zoomed region, thus both limiting the amount of imaging data conveyed and distributing the conveyance of that data over the time of the volume-based navigational session. Ultimately, the doctor typically will zoom until he or she views the feature of interest, which is typically small and of relatively low contrast. At this ultimate point, the system conveys the remainder of the full hierarchy of the unitary pyramidal representation, but only for a relatively small number of voxels of the unitary pyramidal representation which contain the portion of the image including the feature of interest.

Still further, because the disclosed systems and methods employ a voxel-based unitary pyramidal representation, the volume-based navigation can be performed in any direction and for any portion of the image. The volume-based navigation is not biased toward or limited to a slice-based geometry, but rather the doctor can select different viewing angles, fields of view, or other parameters while always taking advantage of the efficient data transfer afforded by the voxel-based unitary pyramidal representation.

Several preferred embodiments have been described herein. Modifications and alterations may occur to others upon reading and understanding the preceding detailed description. It is intended that the description be construed as including all such modifications and alterations insofar as they come within the spirit or scope of the appended claims or the equivalents thereof.

Having thus described the preferred embodiments, the invention is now claimed to be:

1. An image processing system comprising:
 a server including a processor and storage configured to store a unitary pyramidal representation of a volumetric image, the unitary pyramidal representation comprising a set of coefficient voxels and having hierarchical levels where each successive level adds information for providing increased spatial resolution, and each coefficient voxel corresponds to a defined three-dimensional spatial region of the volumetric image and to a selected level of the hierarchy;
 a network interface configured to convey selected coefficient voxels via a network responsive to a request for imaging data of the volumetric image corresponding to a selected spatial region and to a selected spatial resolution; and
 a client including a processor, storage, and a display, the client configured to receive from the server the conveyed selected coefficient voxels and to reconstruct and show on the display an image reconstructed from the received coefficient voxels corresponding to the selected spatial region and the selected spatial resolution;
 wherein the client further includes at least one user input device and is configured to execute an image navigation and processing application program operating in conjunction with the display and the at least one user input device, the executing image navigation and processing application program selecting the spatial region and the spatial resolution, the client further configured to generate and send to the server a client request identifying the selected spatial region and the selected spatial resolution or identifying coefficient voxels corresponding to the selected spatial region and the selected spatial resolution.

2. An image processing system as set forth in claim 1, wherein the client further includes a coefficient voxels cache, the client further configured to identify any cached coefficient voxels corresponding to the selected spatial region and the selected spatial resolution and omitting said cached coefficient voxels from the client request sent to the server.

3. An image processing system as set forth in claim 1, wherein the server is configured to store the unitary pyramidal representation of the volumetric image as a wavelets representation, and wherein each coefficient voxel further corresponds to a selected quadrant or octant of the wavelets representation.

4. An image processing system as set forth in claim 1, wherein the server is configured to generate the unitary pyramidal representation by applying a unitary pyramidal transform along three coordinate directions of a three-dimensional orthogonal coordinate system.

5. An image processing system as set forth in claim 1, wherein the server is further configured to compress the coefficient voxels prior to storing the unitary pyramidal representation.

6. An image processing system as set forth in claim 1, wherein the client is configured to determine the selected spatial resolution based on the spatial region and a display resolution of the display.

7. An image processing system as set forth in claim 1, wherein:
 the volumetric image is four-dimensional including a time dimension, and the server stores the unitary pyramidal representation comprising a set of coefficient voxels and having hierarchical levels each successive level of which adds information providing increased spatial and temporal resolution, and each coefficient voxel corresponds to a defined four-dimensional spatial and temporal region of the four-dimensional volumetric image and to a selected level of the hierarchy;
 the network interface is configured to convey selected coefficient voxels via a network responsive to a request for imaging data of the volumetric image corresponding to a selected spatial and temporal region and to a selected spatial and temporal resolution;
 the client is configured to generate and send to the server a client request identifying the selected spatial and temporal region and the selected spatial and temporal resolution or identifying coefficient voxels corresponding to the selected spatial and temporal region and the selected spatial and temporal resolution; and
 the client is configured to receive from the server the conveyed selected coefficient voxels and to reconstruct and show on the display an image reconstructed from the received coefficient voxels corresponding to the selected spatial and temporal region and the selected spatial and temporal resolution.

8. The image processing system of claim 1 wherein the server is configured to generate the unitary pyramidal representation by operations including:
 transforming the volumetric image into a hierarchical representation comprising a plurality of coefficients, said hierarchical representation comprising a plurality of levels, wherein a level of said hierarchical representation comprises transform data sufficient to reconstruct the volumetric image at a resolution corresponding to said level; and
 partitioning said coefficients into a plurality of voxels, each voxel comprising "n" coefficients in a horizontal direction, "m" coefficients in a vertical direction, and "p" coefficients in a depth direction.

9. An image processing system as set forth in claim 1, wherein the client is configured to determine the selected spatial resolution based on the spatial region and a display resolution of the display.

10. An image navigation and processing method comprising:
 identifying a selected three-dimensional spatial region and spatial resolution for displaying a volumetric image;
 querying a server storing the volumetric image as a unitary pyramidal representation partitioned into coefficient voxels corresponding to defined three-dimensional spatial regions and spatial resolutions of the volumetric image;
 responsive to the query, receiving from the server coefficient voxels of the unitary pyramidal representation containing image data sufficient to reconstruct the selected spatial region of the volumetric image at the selected spatial resolution;
 based on the received coefficient voxels, reconstructing and displaying an image representative of the selected spatial region of the volumetric image at the selected spatial resolution;
 caching coefficient voxels received from the server;
 identifying an update comprising a reduction of the selected three-dimensional spatial region and an increase in the selected resolution;
 update querying the server respective to the update;
 responsive to the update query, receiving from the server additional coefficient voxels that together with the cached coefficient voxels contain image data sufficient to reconstruct the update-reduced selected spatial region of the volumetric image at the update-increased selected spatial resolution, the received additional coefficient voxels also being cached; and
 based on the cached coefficient voxels, reconstructing and displaying an image representative of the update-reduced selected spatial region of the volumetric image at the update-increased selected spatial resolution.

11. A method as set forth in claim 10, further comprising:
 at the server, (i) transforming said volumetric image using a wavelet transform with fixed point kernels to generate the unitary pyramidal representation and (ii) partitioning the unitary pyramidal representation into said coefficient voxels corresponding to defined three-dimensional spatial regions and spatial resolutions of the volumetric image.

* * * * *